US010675096B2

(12) United States Patent
Utz et al.

(10) Patent No.: US 10,675,096 B2
(45) Date of Patent: Jun. 9, 2020

(54) MEDICAL SYSTEM

(71) Applicant: Aesculap AG, Tuttlingen (DE)

(72) Inventors: Michael Utz, Tuttlingen (DE); Franz-Peter Firmbach, Emmingen-Liptingen (DE)

(73) Assignee: Aesculap AG, Tuttlingen (DE)

( * ) Notice: Subject to any disclaimer, the term of this patent is extended or adjusted under 35 U.S.C. 154(b) by 721 days.

(21) Appl. No.: 15/358,799

(22) Filed: Nov. 22, 2016

(65) Prior Publication Data
US 2017/0071677 A1 Mar. 16, 2017

Related U.S. Application Data

(63) Continuation of application No. PCT/EP2015/061621, filed on May 27, 2015.

(30) Foreign Application Priority Data

May 27, 2014 (DE) .................. 10 2014 107 481

(51) Int. Cl.
*A61B 34/20* (2016.01)
*A61B 17/15* (2006.01)
(Continued)

(52) U.S. Cl.
CPC ............ *A61B 34/20* (2016.02); *A61B 17/154* (2013.01); *A61B 17/155* (2013.01);
(Continued)

(58) Field of Classification Search
CPC .............. A61B 34/20; A61B 2017/568; A61B 2034/108; A61B 17/1764; A61B 17/155; A61B 17/157; A61B 2090/3983
See application file for complete search history.

(56) References Cited

U.S. PATENT DOCUMENTS 6,241,735 B1   6/2001  Marmulla
6,327,491 B1 * 12/2001  Franklin ............... A61B 90/11
                                                        600/429
(Continued)

FOREIGN PATENT DOCUMENTS

DE       4219939      10/1995
DE      19747427       5/1999
(Continued)

OTHER PUBLICATIONS

International Search Report for corresponding application No. PCT/EP2015/061621 dated Aug. 19, 2015, 2 pages.

*Primary Examiner* — David W Bates
(74) *Attorney, Agent, or Firm* — Lipsitz & McAllister, LLC

(57) ABSTRACT

The invention relates to a medical system, in particular for implanting a knee joint endoprosthesis, which comprises at least one medical referencing unit whose position in space is detectable using a surgical navigation system. The referencing unit comprises at least one surgical marker element that is arranged or formed on a carrier element and is detectable using a detection device of the surgical navigation system. The at least one referencing unit comprises a base body that carries the carrier element. The base body comprises at least one patient-specific bone contact face faces away from the base body and deviates from being a sector of a surface of a sphere and from being a planar surface. The at least one bone contact face is formed in a manner corresponding to a bone surface of the patient.

20 Claims, 15 Drawing Sheets

(51) Int. Cl.
*A61B 90/00* (2016.01)
*A61B 34/10* (2016.01)
*A61B 17/56* (2006.01)
*B33Y 80/00* (2015.01)

(52) U.S. Cl.
CPC ............ *A61B 17/157* (2013.01); *A61B 90/39* (2016.02); *A61B 2017/568* (2013.01); *A61B 2034/108* (2016.02); *A61B 2034/2055* (2016.02); *A61B 2090/3983* (2016.02); *B33Y 80/00* (2014.12)

(56) References Cited

U.S. PATENT DOCUMENTS

| | | | |
|---|---|---|---|
| 8,444,652 B2 | 5/2013 | Amis et al. | |
| 8,945,132 B2 | 2/2015 | Plassy et al. | |
| 9,364,244 B2 | 6/2016 | Amis et al. | |
| 9,839,846 B2 | 12/2017 | Hughes et al. | |
| 2005/0113846 A1* | 5/2005 | Carson | A61F 2/461 606/130 |
| 2006/0195111 A1 | 8/2006 | Couture | |
| 2007/0066917 A1* | 3/2007 | Hodorek | A61B 90/36 600/595 |
| 2007/0078678 A1* | 4/2007 | DiSilvestro | G06Q 50/22 705/2 |
| 2007/0270718 A1* | 11/2007 | Rochetin | A61B 5/064 600/587 |
| 2008/0195110 A1 | 8/2008 | Plassy et al. | |
| 2008/0319491 A1* | 12/2008 | Schoenefeld | A61B 17/15 606/86 R |
| 2009/0171355 A1 | 7/2009 | Amis et al. | |
| 2011/0257653 A1* | 10/2011 | Hughes | A61B 34/10 606/79 |
| 2012/0277751 A1* | 11/2012 | Catanzarite | A61B 17/155 606/88 |
| 2013/0253524 A1 | 9/2013 | Amis et al. | |
| 2014/0039520 A1 | 2/2014 | Haider et al. | |
| 2014/0096369 A1* | 4/2014 | Matsumoto | A61B 90/39 29/592 |
| 2015/0088141 A1* | 3/2015 | Uthgenannt | A61B 17/1675 606/88 |
| 2015/0182292 A1* | 7/2015 | Hladio | A61B 17/1746 606/87 |
| 2015/0374390 A1 | 12/2015 | Amis et al. | |
| 2018/0153624 A1 | 6/2018 | Hughes et al. | |
| 2018/0368860 A1* | 12/2018 | Wodajo | A61B 17/1703 |

FOREIGN PATENT DOCUMENTS

| | | |
|---|---|---|
| DE | 102010060914 | 5/2012 |
| EP | 1958575 | 8/2008 |
| EP | 2719353 | 4/2014 |
| JP | 2001507614 | 6/2001 |
| JP | 2009530004 | 8/2009 |
| JP | 2010110635 | 5/2010 |
| JP | 2013523415 | 6/2013 |
| WO | 93/25157 | 12/1993 |
| WO | 2012169642 | 12/2012 |

* cited by examiner

MEDICAL SYSTEM

CROSS-REFERENCE TO RELATED APPLICATIONS

This application is a continuation of international application number PCT/EP2015/061621 filed on May 27, 2015 and claims the benefit of German application number 10 2014 107 481.5 filed on May 27, 2014, which are incorporated herein by reference in their entirety and for all purposes.

FIELD OF THE INVENTION

The present invention relates to a medical system, in particular for implanting a knee joint endoprosthesis, comprising at least one medical referencing unit whose position in space is capable of being detected using a surgical navigation system, which referencing unit comprises at least one surgical marker element that is arranged or formed on a carrier element and is capable of being detected using a detection device of the surgical navigation system, which at least one referencing unit comprises a base body that carries the carrier element.

BACKGROUND OF THE INVENTION

Such a system is known, for example, from DE 10 2010 060 914 A1. In order to position one or more medical referencing units on a patient's body, it is necessary at the start of a navigationally assisted operation first to record landmarks on the patient's body, for example by navigationally assisted palpation of characteristic points. Moreover, if image data of the patient's anatomy exist before the intervention, it is difficult for these image data to be brought into accordance with landmarks or characteristic points on the patient's body that have been determined in a navigationally assisted manner. In particular, this takes up a great deal of time at the start of a surgical intervention and is therefore associated with considerable cost.

By the term "surgical marker element" as used in the present patent application, it is meant to include in particular a defined reference point, for example in the form of a defined depression whose position on the carrier element is known. Such a reference point may, for example, be palpated with a navigated palpation instrument. The reference point can thereby be assigned its position in space by determining the position of the palpation instrument in space. If a bone has fixed thereto a further referencing unit comprising at least one, preferably three, surgical marker elements, then the position of the defined reference point with respect to the further referencing unit is also known so that even when the bone with the carrier element thereon is moved, a position of the defined reference point is capable of being determined at any time via the navigation system by determining the location and orientation of the further referencing unit.

SUMMARY OF THE INVENTION

In an aspect of the invention, a medical system, in particular for implanting a knee joint endoprosthesis, comprises at least one medical referencing unit whose position in space is detectable using a surgical navigation system. The referencing unit comprises at least one surgical marker element that is arranged or formed on a carrier element and is detectable using a detection device of the surgical navigation system. The at least one referencing unit comprises a base body that carries the carrier element. The base body comprises at least one patient-specific bone contact face faces away from the base body and deviates from being a sector of a surface of a sphere and from being a planar surface. The at least one bone contact face is formed in a manner corresponding to a bone surface of the patient.

BRIEF DESCRIPTION OF THE DRAWINGS

The foregoing summary and the following description may be better understood in conjunction with the drawing figures, of which.

DETAILED DESCRIPTION

Figure 1:
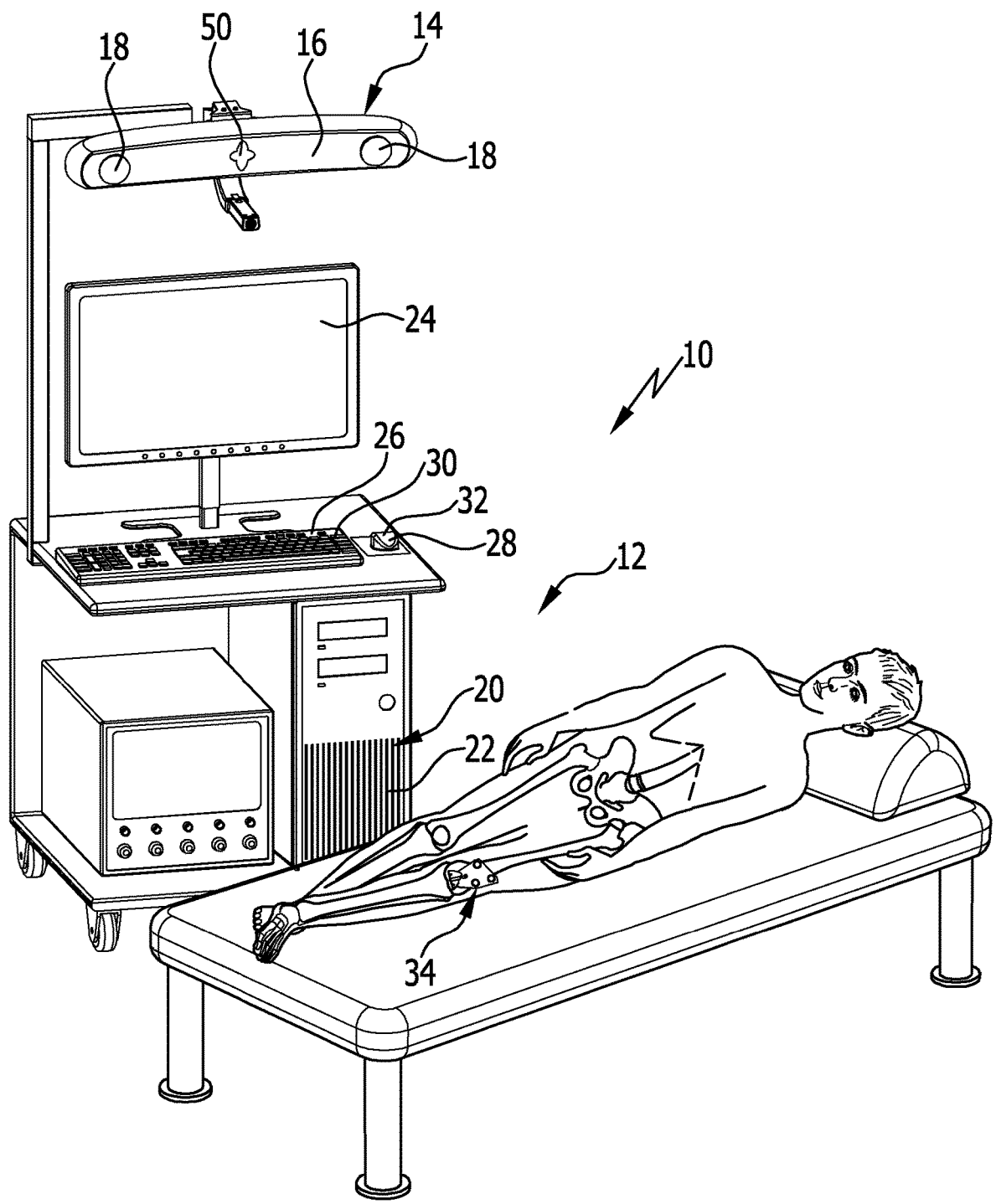
FIG. 1 illustrates a schematic general view of an exemplary embodiment of a medical system comprising, in particular, a surgical navigation system.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical system, in particular for implanting a knee joint endoprosthesis, comprising at least one medical referencing unit whose position in space is detectable using a surgical navigation system, which referencing unit comprises at least one surgical marker element that is arranged or formed on a carrier element and is detectable using a detection device of the surgical navigation system, which at least one referencing unit comprises a base body that carries the carrier element, wherein the base body comprises at least one patient-specific bone contact face facing away from the base body and deviating from being a sector of a surface of a sphere and from being a planar surface, said at least one bone contact face being formed in a manner corresponding to a bone surface of the patient.

The proposed improvement makes it possible for the at least one referencing unit to be easily and safely placed in a defined manner in contact against and optionally fixed to a patient's bone in particular. A unique positioning of the at least one referencing unit on the patient's bone can thus be ensured, in particular when the patient-specific bone contact face is produced on the basis of image data of the patient's bone. In this case, there is no more need for additional assignment and referencing of the position of the at least one referencing unit on the patient's body at the start of the surgical intervention. In a sense, this step is accomplished in the fact that, on the basis of the configuration of the patient-specific bone contact face and with knowledge of the position of the at least one surgical marker element relative to the patient-specific bone contact face, any referencing at the start of the surgical intervention would be redundant. Preferably, the patient-specific bone contact face has a size of at least 3 cm$^2$. It is advantageous for the patient-specific bone contact face to be even larger than that, for example at least 6 cm$^2$. The larger the patient-specific bone contact face, the more safely and the more uniquely can an accurate positioning of the at least one referencing unit on the patient's body be achieved. The system can be used in particular for the implantation of artificial joints, such as artificial knee, hip or shoulder joints. This list is non-exhaustive.

It is preferred for the base body and the carrier element to be of one-piece configuration or to be non-releasably connected together. This prevents a change in a relative position between the carrier element and the base body and hence between the at least one marker element and the patient-specific bone contact face from being produced directly and by a surgeon or the surgeon's assistant staff, either intentionally or unintentionally. Overall, it is thus possible to minimize an error-proneness of the system.

Furthermore, it may be advantageous for the base body and the carrier element to be configured for releasable connection to each other. The carrier element with the at least one marker element thereon can thereby be used multiple times. It is then only necessary to manufacture, for each patient, one or more base bodies with patient-specific bone contact faces which can then be connected to the carrier element.

It is advantageous for the system to comprise a coupling device for force-locking and/or form-locking coupling of the base body and the carrier element in a coupling position. With such a coupling device, the base body and the carrier element can be connected together in a defined manner. In particular, the coupling device may be configured to enable between the base body and the carrier element a unique coupling, i.e. a coupling that can occur in only a single way.

A particularly simple configuration of the coupling device can be achieved by the coupling device comprising first and second coupling elements which are arranged or formed on the base body on the one hand and the carrier element on the other hand and are in engagement when in the coupling position and are out of engagement when in an uncoupling position.

For a simple and safe coupling of the base body and the carrier element, it is advantageous for the first and second coupling elements to comprise at least one coupling receptacle and a corresponding coupling projection cooperating therewith. Provision may be made for there to be two or more coupling receptacles or two or more coupling projections that are arranged or formed on either the carrier element or the base body or both.

In accordance with another preferred embodiment of the invention, provision may be made for the at least one referencing unit to comprise at least one fastening element receptacle for a fastening element for fixing the referencing unit to a bone. Such a referencing unit can be easily and safely fixed to a bone in a defined manner.

It is preferred for the at least one fastening element receptacle to be arranged or formed on the base body and/or on the carrier element. In particular, this enables the base body or the carrier element to be fixed to the patient's bone separately from one another and optionally together using one or more fastening elements.

The at least one fastening element receptacle is particularly simple to produce when it is configured in the form of an opening. In particular, it may be configured in the form of a bore. In order to prevent a change in position of the base body or of the carrier element, it is advantageous for a sleeve extending the opening to be arranged or formed on the base body and/or on the carrier element. This sleeve provides particularly good guidance therewithin for a bone pin, a bone screw or a bone nail. The sleeve can in particular also predetermine and indicate to a surgeon a direction for inserting the bone fastening element.

In accordance with another preferred embodiment of the invention, provision may be made for the medical system to comprise at least one medical instrument which is capable of being releasably connected to the at least one referencing unit. This configuration makes it possible, for example, for one or more instruments to be connected to the referencing unit. If the latter is fixed to the patient's body in a defined manner, then by connecting the at least one medical instrument to the at least one referencing unit in a defined manner, the at least one medical instrument, too, can be fixed to the patient's body in a uniquely predetermined manner.

A particularly simple way of providing for a releasable connection between the at least one medical instrument and the at least one referencing unit is for the medical system to comprise a coupling device for force-locking and/or form-locking coupling of the at least one medical instrument and the at least one referencing unit in a coupling position.

It is advantageous for the coupling device to comprise first and second coupling elements which are arranged or formed on the at least one referencing unit on the one hand and on the at least one medical instrument on the other hand and are in engagement when in the coupling position and are out of engagement when in an uncoupling position. In particular, it is advantageous for at least one coupling element of the coupling device to be arranged or formed on the base body of the at least one referencing unit. This allows the at least one medical instrument to be coupled to the base body of the referencing unit. When the carrier element in particular is capable of being separated from the base body, it is thus optionally also possible for the carrier element with the at least one marker element thereon to be removed, while the base body can still remain fastened to the patient's body.

A simple and safe way of connecting together the at least one referencing unit and the at least one medical instrument is for the first and second coupling elements to comprise at least one coupling receptacle and at least one corresponding coupling receptacle cooperating therewith.

In particular, the coupling receptacle and the coupling projection may be configured to enable a force-locking and/or form-locking connection therebetween.

In order to enable the medical instrument to be optionally fixed to a patient's bone independently of the at least one referencing unit, it is advantageous for the at least one medical instrument to comprise at least one instrument fastening element receptacle for a fastening element for fixing the at least one medical instrument to a bone.

The at least one instrument fastening element receptacle is preferably configured in the form of an opening. In particular, such an opening can be easily produced, for example in the form of a bore.

In accordance with another preferred embodiment of the invention, provision may be made for the at least one medical instrument to comprise a contact body comprising at least one patient-specific contact body bone contact face facing away from the contact body and deviating from being a sector of a surface of a sphere and from being a planar surface, said at least one patient-specific contact body bone contact face being formed in a manner corresponding to a bone surface of the patient. With this configuration, it is in particular possible for the at least one medical instrument to be placed against and optionally fixed to a patient's bone at a specific location thereof in a unique and defined manner. The at least one medical instrument can thereby be fixed to the bone in a manner, position and, optionally, orientation that are determined before a surgical intervention is performed.

It is advantageous for the at least one fastening element receptacle and the at least one instrument fastening element receptacle each to define a longitudinal axis, said longitudinal axes coinciding in the coupling position. This configuration makes it possible for the at least one referencing unit on the one hand and the at least one medical instrument on the other hand to be fixed to the bone of a patient with only a single fastening element. In particular, the fastening element can simultaneously extend both through the at least one fastening element receptacle and the at least one instrument fastening element receptacle.

It is advantageous for the at least one medical instrument to comprise a saw template for a femur and/or a tibia. With a saw template fixed to the bone of a patient in a unique manner as described, either on the femur and/or on a tibia of the patient, it is possible prior to performing a surgical intervention, for example when preparing femur and/or tibia for the implantation of a component of a knee joint endoprosthesis, to make unique and predefined saw cuts which enable optimal adaptation of the prosthesis component to the bone.

It is advantageous for the saw template to comprise at least one saw slot for a saw blade of a bone saw. In particular, it is advantageous for the saw template to comprise two or more saw slots. With this construction, it is only necessary for one saw template to be fixed to the patient's bone, and two or more saw cuts can then be made on the bone.

It is advantageous for the patient-specific bone contact face and/or the patient-specific contact body bone contact face to have a contour which corresponds to at least a part of a bone surface of a femur or tibia. The at least one medical instrument can thus be placed in contact against and optionally fixed to a patient's femur or tibia in a defined manner.

In accordance with another preferred embodiment of the invention, provision may be made for the patient-specific bone contact face and/or the patient-specific contact body bone contact face and/or the base body and/or the contact body to be manufactured by casting, moulding, chip-producing machining methods, selective laser sintering, additive manufacturing methods or 3-D printing. The aforementioned possibilities for manufacture are purely illustrative and not limiting in nature. Any other fabrication techniques familiar to the person skilled in the art can be used in order to form parts of the system with patient-specific contact faces.

It is advantageous for the patient-specific bone contact face to define bone contact face contour data which correspond or substantially correspond to non-invasively determined bone contour data of the patient. The patient's bone contour data can be derived, for example, from X-ray, magnetic resonance and/or ultrasound images. Thus, the patient-specific bone contact face can be individually adapted to the bone of a particular patient making use of available bone contour data. The aforementioned possibilities for non-invasive determination of the patient's bone contour data are purely illustrative and not limiting in nature. Other types of techniques for non-invasive determination of bone contour data familiar to the person skilled in the art are conceivable.

Furthermore, it is advantageous for the patient-specific contact body bone contact face to define contact body bone contact face contour data that correspond or substantially correspond to non-invasively determined bone contour data of the patient. In particular, the non-invasively determined bone contour data of the patient can also be derived from X-ray, magnetic resonance and/or ultrasound images of particular bones of the patient.

It is preferred for the medical system to comprise at least one fastening element for fixing the referencing unit to a bone. Preferably, the medical system comprises two or more fastening elements of the kind mentioned. The at least one referencing unit and/or the at least one medical instrument can thus be fixed to the patient's bone in a defined and safe manner.

A particularly cost-effective way to configure the medical system is to configure the at least one fastening element in the form of a bone screw or in the form of a bone pin or in the form of a bone nail. Of course, alternatively, other fastening elements familiar and known to the person skilled in the art can also be used in order to fix the at least one referencing unit and/or the at least one medical instrument to a bone in a defined and safe manner.

In order for a position in space of the at least one referencing unit to be determined in a unique manner, it is advantageous for the at least one medical referencing unit to comprise at least three marker elements. It may also comprise four, five or even more marker elements. In particular, the use of more than three marker elements allows the accuracy of position determination of the at least one referencing element in space to be improved. For example, having additional marker elements can provide for position determination to be effected in a partially redundant manner. Moreover, for example, it provides the option of a damaged or contaminated marker element to be detected and ignored in the position determination of the at least one referencing unit without compromising accurate position determination of the at least one referencing unit in space.

In accordance with a further preferred embodiment of the medical system, it is advantageous for the medical system to comprise a surgical navigation system comprising at least one detection device for detecting the position of the at least one referencing unit. For example, arrangements of the at least one marker element on the carrier element of the at least one referencing unit or bone contour data of the patient and hence data of the patient-specific contact body bone contact faces or of the patient-specific bone contact face can be stored in a processing or storage unit of the navigation system in order to thus optimize use of the at least one referencing unit and of the at least one medical instrument, in particular in terms of their accuracy.

FIG. 1 illustrates an example of a medical system 10. In particular, the medical system 10 comprises a navigation system 12 comprising a receiving unit 14 in the form of a stereoscopic camera 16 comprising two detectors 18 which are preferably configured for detecting electromagnetic radiation in the near-infrared (NIR) region. In particular, their detection range may be in a wavelength range from approximately 820 nm to approximately 880 nm.

The navigation system 12 further comprises data processing equipment 20 which in the exemplary embodiment as depicted in FIG. 1 comprises a computer 22, a monitor 24 and input devices 26 and 28 in the form of a keyboard 30 and a mouse 32. The computer 22 is coupled to the monitor 24, the input devices 26 and 28 and the receiving unit 14.

The data processing equipment 20 allows signals received by the receiving unit 14 to be processed in order for a position and/or orientation in space of a referencing unit 34 to be determined. The monitor allows in particular the location and orientation of the referencing unit 34 to be displayed in the operating room.

Figure 2:
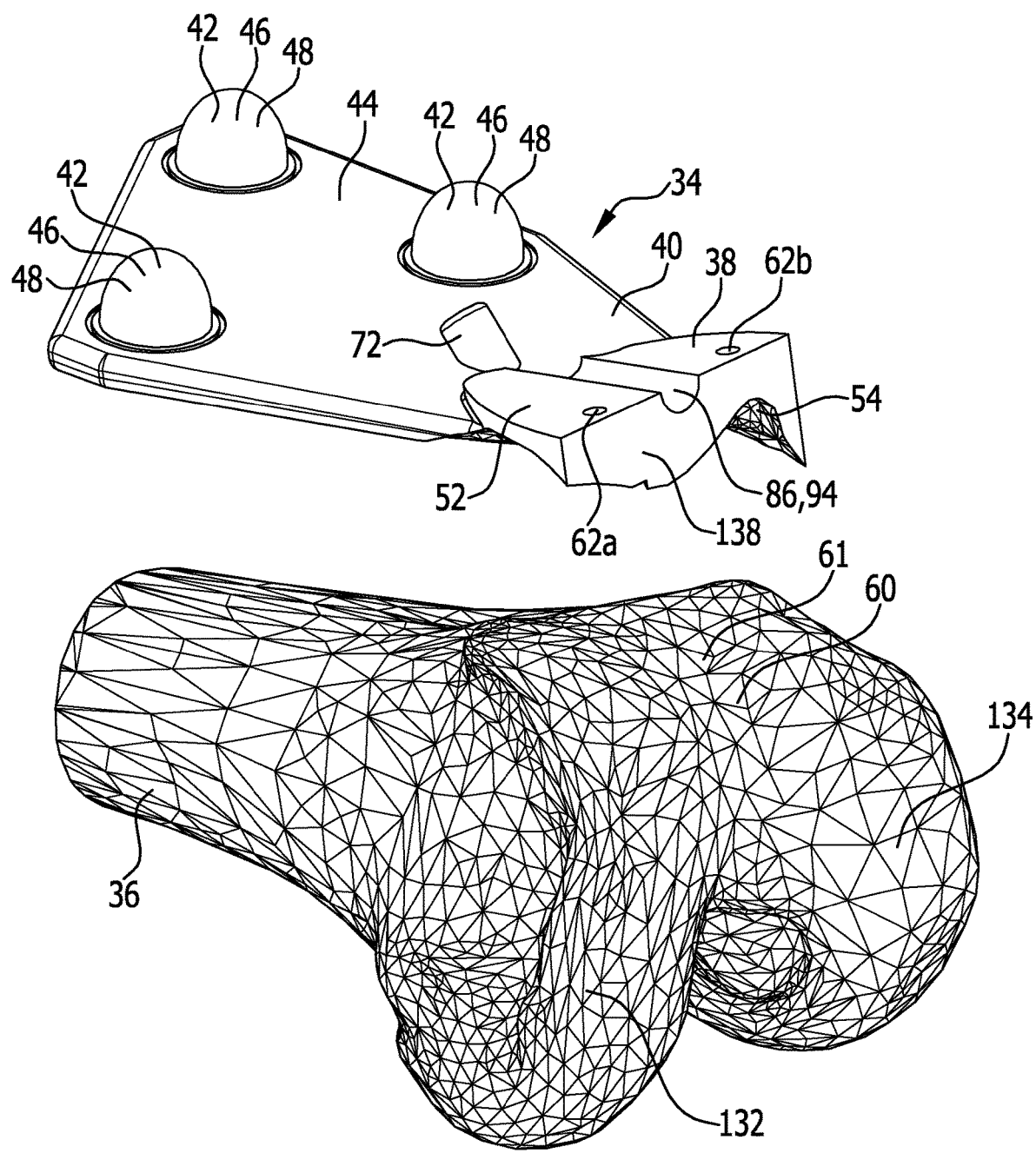
FIG. 2 illustrates a schematic representation of a first exemplary embodiment of a referencing unit having a patient-specific bone contact face, shown in the process of being brought into contact against a femur.
Figure 3:
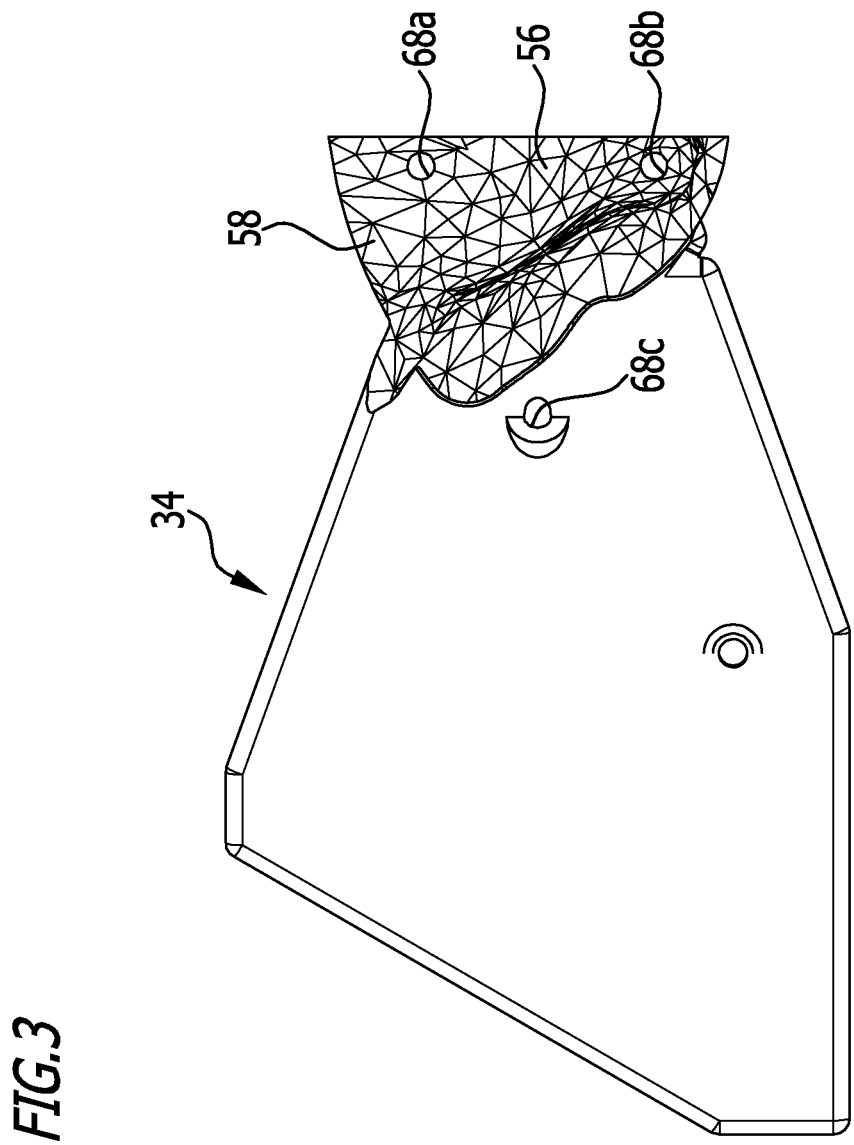
FIG. 3 illustrates a bottom view of the referencing unit from FIG. 2.

The referencing unit 34 is schematically shown in FIG. 2 prior to being placed in contact against a femur 36. It comprises a base body 38 which carries a carrier element 40 comprising marker elements 42. In the referencing unit 34 as illustrated in FIG. 2, the carrier element 40 is configured in the form of a polygonal carrier plate 44 on which the marker elements 42 are arranged. These are configured in the form of hemispheres 46 whose surfaces 48 reflect electromagnetic radiation or ultrasound which is emitted for example from an emitter 50 of the navigation system 12.

Alternatively, instead of being implemented in a passive configuration as described above, the marker elements 42 may also be configured in the form of active marker elements which emit for example electromagnetic radiation or ultrasound.

In lieu of the marker elements 42, defined reference points may be provided on the carrier element 40, for example in the form of defined depressions whose position on the carrier element is known. Said reference points may, for example, be palpated with a navigated palpation instrument which comprises at least three marker elements capable of being detected by the stereoscopic camera 16. Thus, the reference points can be assigned their position in space by determining the position of the palpation instrument in space. If the femur 36 has fixed thereto a further referencing unit, not illustrated in the figures, comprising at least one, preferably three, surgical marker elements, then the position of the defined reference points relative to the further referencing unit is also defined so that when the femur 36 with the carrier element thereon is moved, a position of the defined reference points is capable of being determined at any time via the navigation system by determining the location and orientation of the further referencing unit.

The arrangement of the marker elements 42 relative to each other is preferably stored in a storage of the data processing equipment 20. The position of the individual marker elements 42 in space and hence the location and orientation of the referencing unit 34 as a whole can then be determined by way of the navigation system 12 in a known manner.

In the referencing unit 34 of FIG. 2, the base body 38 and the carrier element 40 are non-releasably connected together. Alternatively, they can be configured in one piece.

The base body 38 has a planar upper side 52 and a bottom side 54. The bottom side 54 is configured in the form of a patient-specific bone contact face 56 that faces away from the base body 38 and deviates from being a sector of a surface of a sphere and from being a planar surface. A contour 58 of the bone contact face 56 corresponds to a part 61 of a bone surface 60 of the femur 36.

Figure 4:
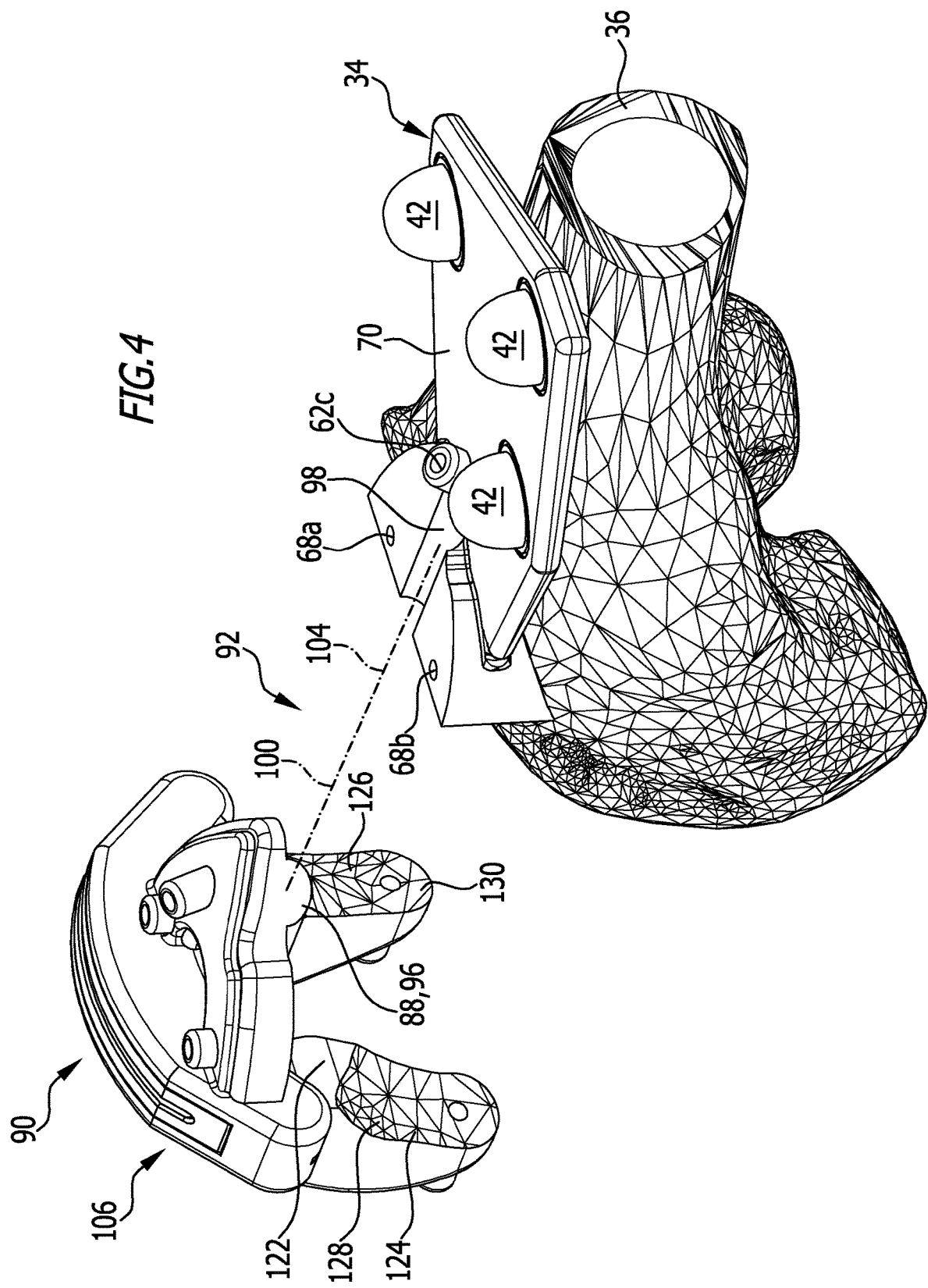
FIG. 4 illustrates a schematic representation of a first exemplary embodiment of a medical instrument in the form of a saw template shown before being brought into contact against and coupled to the referencing unit of FIG. 2 placed in contact against the bone.
Figure 5:
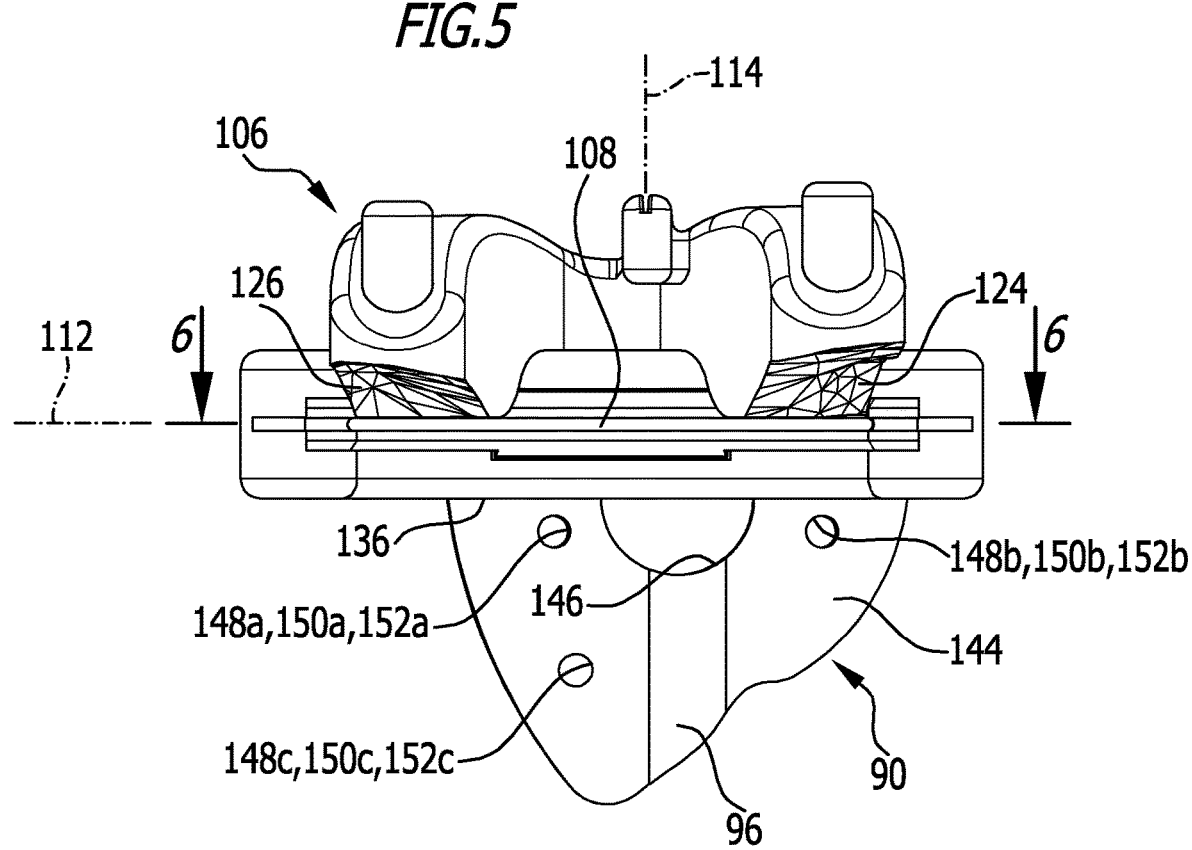
FIG. 5 illustrates a bottom view of the medical instrument from FIG. 4.
Figure 6:
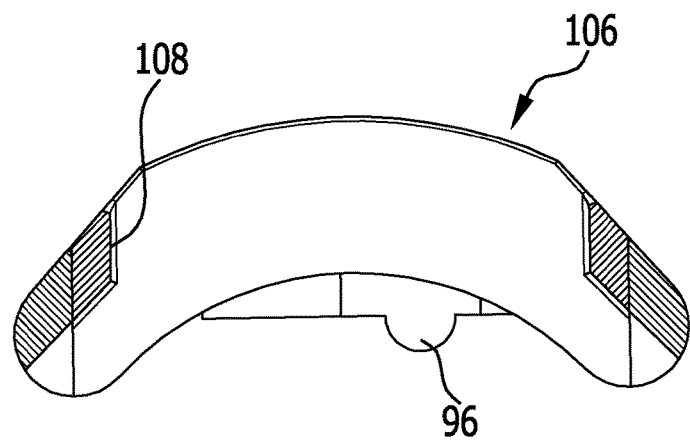
FIG. 6 illustrates a sectional view taken along line 6-6 in FIG. 5.

Based on the contour 58 of the bone contact face 56 that is adapted to the bone surface 60, there exists exactly one possibility of placing the base body 38 in contact against the femur 36 in a precisely fitting relationship therewith. That position of the referencing unit 34 on the femur 36 is illustratively depicted in FIG. 4.

Furthermore, the referencing unit 34 is provided with fastening element receptacles 62a, 62b and 62c. Each of these serves to receive a fastening element 64 for fixing the referencing unit 34 to the femur 36.

The fastening element receptacles 62a, 62b and 62c are configured in the form of openings 66a, 66b and 66c, namely in the form of bores 68a, 68b and 68c. The bores 68a and 68b extend transversely, in particular perpendicularly, to the upper side 52 and extend through the bone contact face 56.

The bore 68c is formed in the area of the carrier plate 44 and extends through the carrier element 40. The opening 66c of the carrier plate 44 is somewhat extended by way of a sleeve 72 projecting from an upper side 70 of the carrier element 40, said sleeve 72 defining a longitudinal axis that extends in skew relation to the longitudinal axes of the bores 68a and 68b.

The fastening elements 64 are configured in the form of bone pins 74 comprising a tip 76 which is adjoined by a short external thread section 78 in the form of a bone thread. Adjoining the external thread section 78 is a cylindrical shaft section 80 that is somewhat longer than half the total length of the bone pin 74.

Formed at an end of the bone pin 74 opposite the tip 76 thereof is a polygonal section 82 which in the case of the bone pins 74 illustrated in the figures is configured in the form of a trigon. A length of the polygonal section 82 parallel to a longitudinal axis 84 defined by the bone pin 74 corresponds approximately to a length of the external thread section 78.

An external diameter of the shaft section 80 is adapted to an internal diameter of the bores 68a, 68b and 68c so that the bone pins 74 can extend with the shaft section 80 thereof through the openings 66a, 66b and 66c in a manner essentially free from play.

Furthermore, the base body 38 has a first coupling element 86 formed thereon in a manner that corresponds to a second coupling element 88 of a medical instrument 90. The coupling elements 86 and 88 form a coupling device 92 for force-locking and/or form-locking coupling of the medical instrument 90 and the referencing unit 34 in a coupling position.

The first coupling element 86 is in the form of a coupling receptacle 94, and the second coupling element 88 is in the form of a corresponding coupling projection 96 cooperating therewith. The coupling receptacle 94 is configured in the form of a groove defining a longitudinal axis 100, said groove defining a cross-section of semi-circular shape. The coupling projection 96 is configured in the form of a rib 102 of semi-cylindrical shape whose longitudinal axis 104 runs parallel to the longitudinal axis 100.

The instrument 90 comprises a saw template 106 for the femur 36. The saw template 106 comprises two saw slots 108 and 110 which define cutting planes 112 and 114 extending perpendicularly to one another.

The instrument 90 further comprises a substantially U-shaped contact body 116 which carries, on a front side 118 thereof, a projecting slot body 120 through which the saw slot 110 extends.

Formed on a rear side 122 of the contact body 116, in the area of free ends thereof, are two contact body bone contact faces 124 and 126 having contours 128 and 130 which correspond to portions or parts 132 and 134 of the bone surface 60 of the femur 36.

Formed between the contact body bone contact faces 124 and 126 is a planar stop face 136 which, in the coupling position, is in contact against a planar end face 138 of the base body 38.

A second slot body 140 has the saw slot 108 extending therethrough and is arranged in a connecting area between free legs of the contact body 116. It carries a coupling body 142 having a planar bottom side 144 from which the coupling projection 96 projects. The coupling body 142 is substantially configured in the shape of a half ring and together with the second slot body 140 delimits an opening 146 of substantially semi-circular shape.

The bottom side 144 is in surface contact against the upper side 52 of the base body 38 when in the coupling position.

Furthermore, the coupling body 142 has three instrument fastening element receptacles 148a, 148b and 148c which are configured in the form of openings 150a, 150b and 150c, namely in the form of bores 152a, 152b and 152c.

Figure 7:
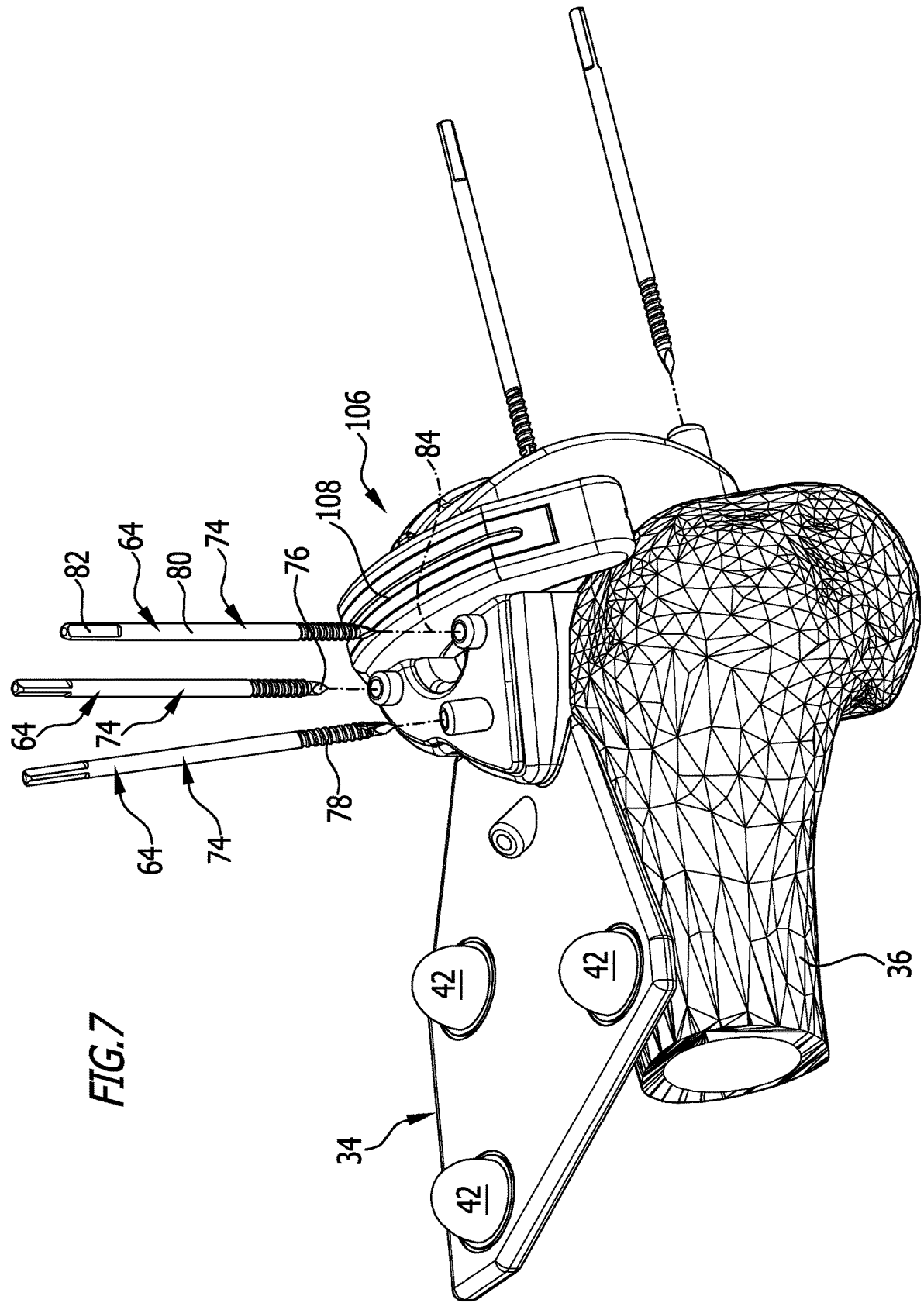
FIG. 7 illustrates a schematic perspective view of the referencing unit placed in contact against the femur and of the instrument of FIG. 4 placed in contact against the femur, shown in the process of being fixed by way of bone pins.
Figure 8:
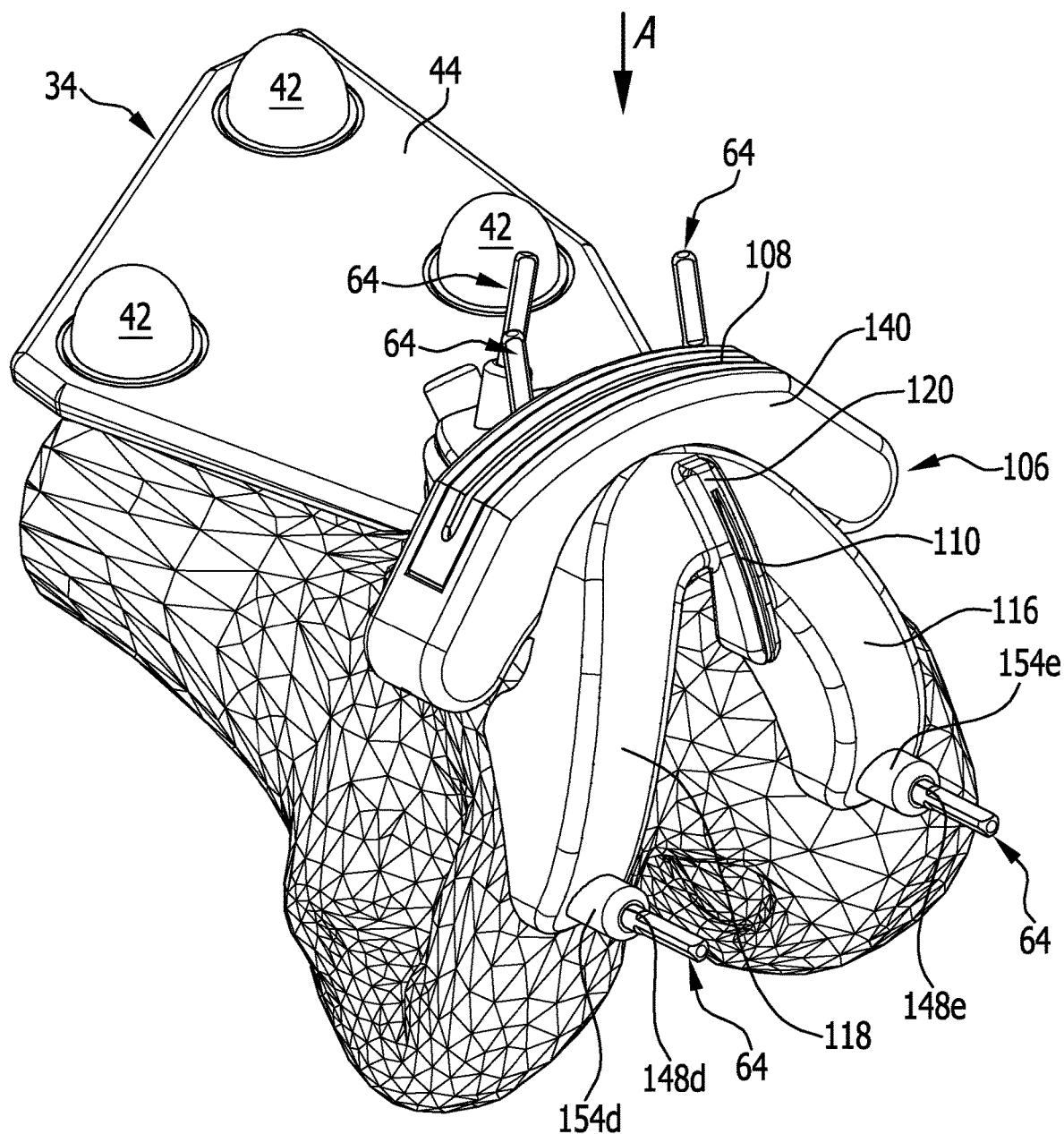
FIG. 8 illustrates a perspective view of the coupled unit of the referencing unit and the medical instrument after fixing to the femur.
Figure 9:
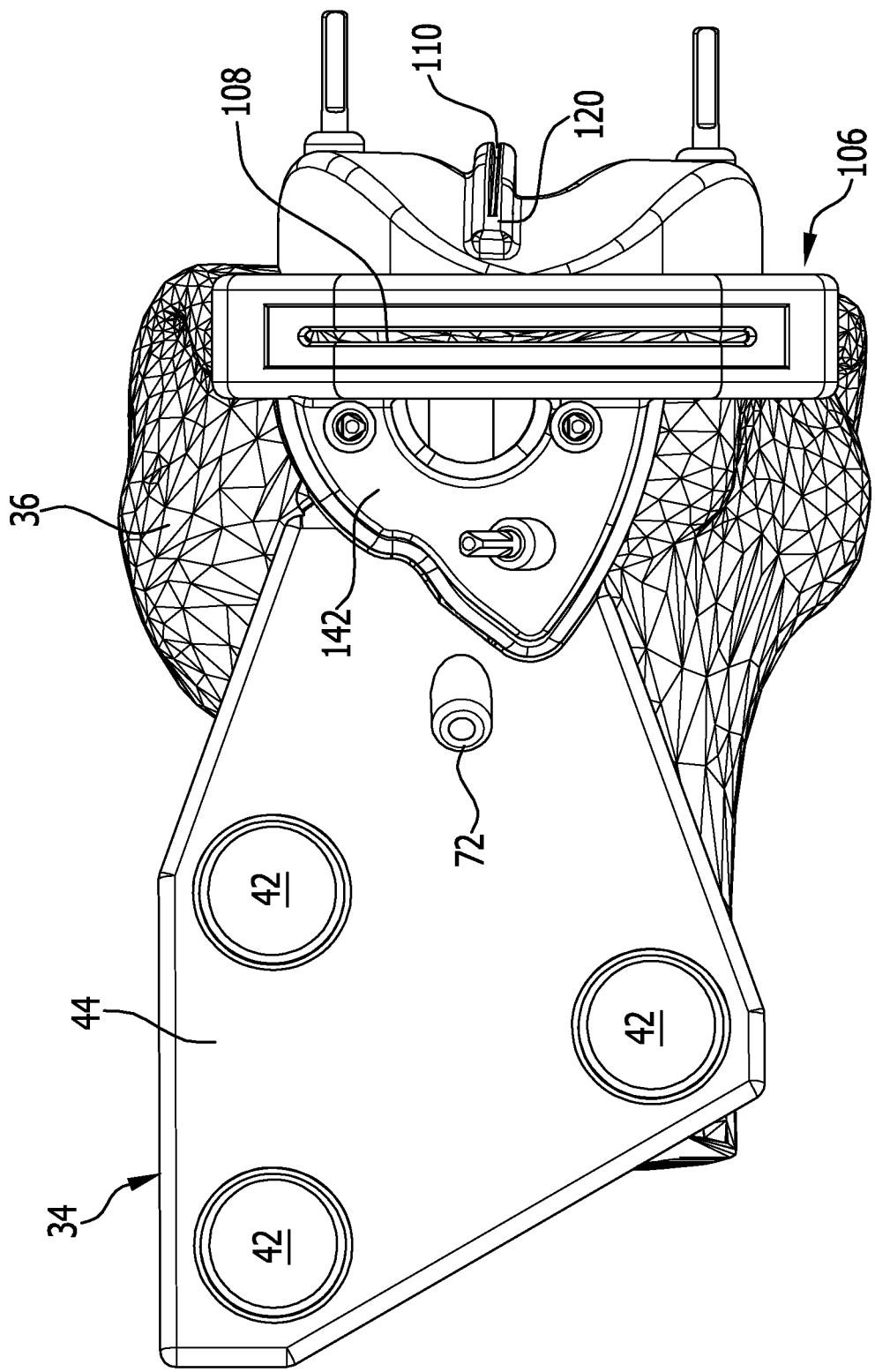
FIG. 9 illustrates a view of the arrangement of FIG. 8 taken in the direction of arrow A.

In the coupling position, longitudinal axes of the bores 152a and 152b coincide with longitudinal axes of the bores 68a and 68b. This allows for the referencing unit 34 and the instrument 90 to be fixed to the femur by way of two fastening elements 64 when in the coupling position. This is schematically depicted in FIGS. 7 to 9.

In order to be able to additionally fix the instrument 90 to the femur 36, the contact body 116 has provided thereon two further instrument fastening element receptacles 148d and 148e which extend through the contact body bone contact faces 124 and 126.

The instrument fastening element receptacles 148d and 148e are also extended by short sleeves 154d and 154e. Longitudinal axes of the instrument fastening element receptacles 148d and 148e extend essentially parallel to each other and define a plane that extends perpendicularly to a plane spanned by longitudinal axes of the instrument fastening element receptacles 148a and 148b. The last-named plane further extends parallel to the cutting plane 112. The plane spanned by the instrument fastening element receptacles 148d and 148e further extends perpendicularly to the cutting plane 114.

The patient-specific bone contact face 56 defines bone contact face contour data that correspond to non-invasively determined bone contour data of the patient. To this end, in particular, the patient's bone contour data from X-ray, magnetic resonance and/or ultrasound images can be utilized.

Based on the patient's bone contour data thus determined in a non-invasive manner, the patient-specific bone contact face 56 or the base body 38 can be manufactured by, for example, casting, moulding, chip-producing machining methods or 3-D printing. Thus, this means that for the surgical intervention, a base body 38 is configured that is individually adapted to a contour of the femur 36 of the patient. In this way, the non-invasively determined bone contour data of the patient result in a unique positioning of the referencing unit 34 on the femur 36.

The contact body 116, or the entire instrument 90, with the contact body bone contact faces 124 and 126 thereof is configured analogously to what has been described above. The patient-specific contact body bone contact face defines contact body bone contact face contour data that correspond to non-invasively determined bone contour data of the patient. These bone contour data of the patient, too, can be derived in particular from X-ray, magnetic resonance and/or ultrasound images.

Overall, it is thus possible to provide for unique positioning of the instrument 90 on the femur 36. Moreover, because the coupling device 92 predetermines a unique spatial relationship between the referencing unit 34 and the instrument 90 when in the coupling position, the cutting planes 112 and 114 that are predetermined by the surgeon, in particular on the basis of the non-invasively determined image data, are defined uniquely and individually for the respective patient by way of the saw slots 108 and 110.

The fixing of the referencing unit 34 and the medical instrument 90 for preparation of the femur 36 for implantation of a femoral component of a knee joint endoprosthesis is explained below.

First, the referencing unit 34 is brought with the bone contact face 56 thereof to the part 61 of the bone surface 60 so that the referencing unit 34 is in contact against the femur 36 in a unique manner. The referencing unit 34 is pre-fixed to the femur 36 using two bone pins 74. To this end, the bone pins 74 are inserted through the fastening element receptacles 62a and 62b.

Optionally, in order to additionally prevent rotation of the referencing unit 34 relative to the femur 36, a further bone pin 74 can be inserted through the fastening element receptacle 62c and driven into the femur 36. This is recommendable in particular where the referencing unit 34 is to be used by itself, i.e. without the instrument 90, for example for determining a location and orientation of the femur 36 in space.

Via the bone pins 74 projecting from the femur 36 in parallel relation to each other and extending through the openings 66a and 66b, it is now possible for the instrument 90 to be brought to the femur 36. To this end, the coupling body 142 is brought to the polygonal sections 82 of the bone pins 74 previously set in position, and these are then passed through the bores 152a and 152b.

In order to prevent displacement of the instrument 90 relative to the femur 36 and to the referencing unit 34, two further bone pins 74 are inserted through the instrument fastening element receptacles 148d and 148e and anchored in the femur 36.

In order to carry out saw cuts on the femur 36 using the instrument 90, the referencing unit 34 can be optionally removed from the femur 36 without the instrument 90 having to be removed. To this end, the two bone pins 74 that extend through the bores 152*a* and 152*b* are removed from the femur 36 so that the referencing unit 34 can be withdrawn from between femur 36 and contact body 116.

Alternatively, it is also possible for the instrument 90 and the referencing unit 34 to be configured such that the instrument 90 is capable of being removed from the femur 36 so that the referencing unit 34 alone can remain in place on the femur 36 in order, for example, to continue tracking the location and orientation thereof in space. To this end, in particular once the saw cut has been made, the instrument 90 can, after removing the two bone pins 74 inserted through the instrument fastening receptacles 148*e* and 148*d*, be removed from the femur 36 and from the two bone pins 74 inserted through the bores 68*a* and 68*b*. The referencing unit 34 then remains in what is called a "parked" position.

Optionally, the instrument 90 and the referencing unit can be placed in contact against the femur 36 together instead of in the order described.

Alternatively, it is also possible to first place the instrument 90 with the contact body bone contact faces 124 and 126 thereof into contact against the femur 36 and fix it thereto and only then couple the instrument 90 to the referencing unit 34.

For a good fixation of the instrument 90 to the femur 36, the two bone pins 74 that had been removed can be inserted again. Alternatively or additionally, it is also possible for a bone pin 74 to be inserted in the bore 152*c* and anchored in the femur 36, wherein a longitudinal axis of the bore extends at a skew angle relative to the longitudinal axes of the bores 152*a* and 152*b*.

After the desired cuts have been made on the femur 36 with a saw, all of the bone pins 74 and the medical instrument 90 can be removed again from the femur.

It is possible for the instrument 90 to be replaced with a further instrument, not shown in the figures, in order to carry out further saw cuts on the femur 36.

With the femur 36 now prepared, a femoral component of a knee joint endoprosthesis, not illustrated in the figures, can be placed thereagainst and suitably affixed thereto, for example by way of bone screws and/or bone cement.

Both the referencing unit 34 and the medical instrument 90 may be made entirely from a sterilizable plastics material, such as polyetheretherketone (PEEK) or polyamide 12 (PA 12).

Optionally, it is also conceivable for the base body 38 and the carrier element 40 to be configured for releasable connection to one another. To that end, there may be provided a coupling device, not depicted in the figures, comprising first and second coupling elements which are arranged or formed on the base body 38 on the one hand and on the carrier element 40 on the other hand. This then allows for the base body 38 and the carrier element 40 to be temporarily connected together in a manner similar to the coupling device 92. In particular, this makes it possible for the carrier element 40 with the marker elements 42 thereon to be separated from the base body 38. Thus, for example, the carrier element 40 with the marker elements 42 thereon can be used multiple times and only the base body 38 with the patient-specific bone contact face 56 thereof need be fabricated in a patient-specific manner for the surgical intervention. It is thus possible to additionally reduce costs.

Figure 10:
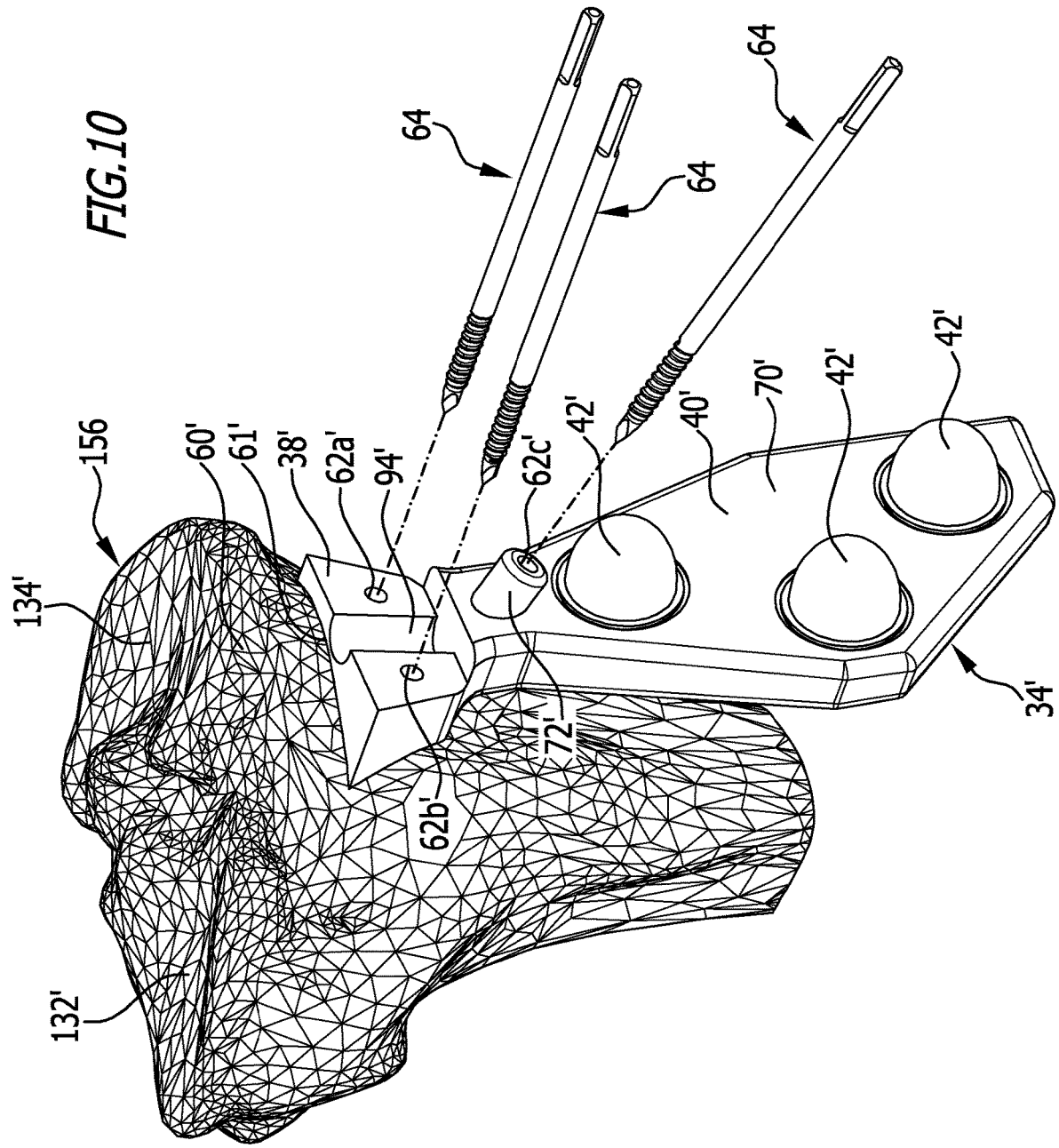
FIG. 10 illustrates a perspective schematic view of a further exemplary embodiment of a medical referencing unit, shown being placed into contact against and fixed to a tibia.
Figure 11:
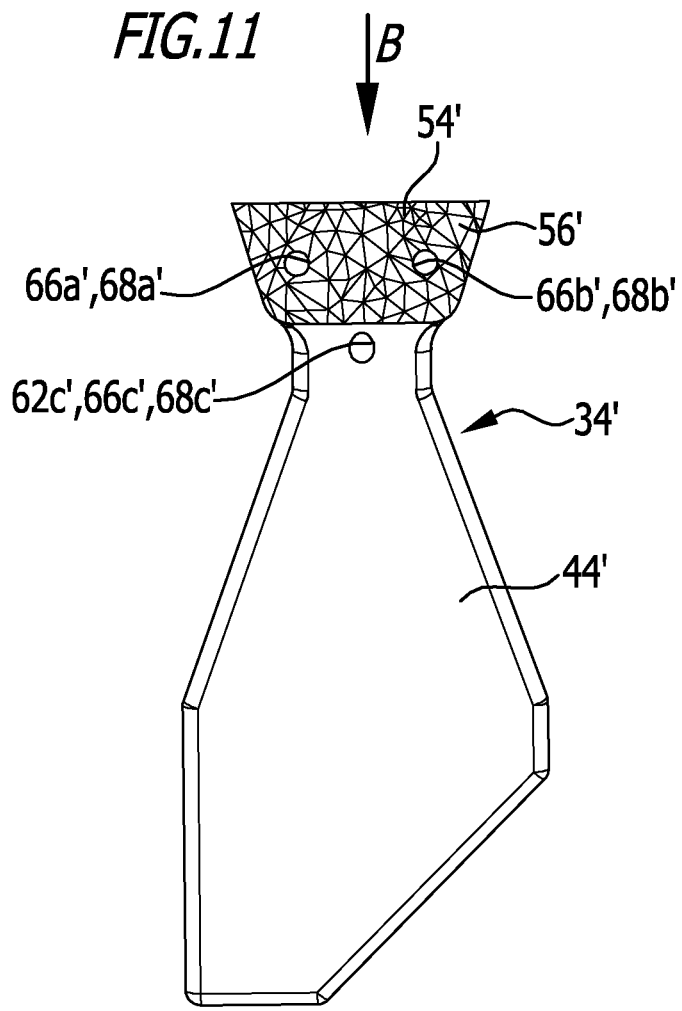
FIG. 11 illustrates a bottom view of the referencing unit of FIG. 10.
Figure 12:
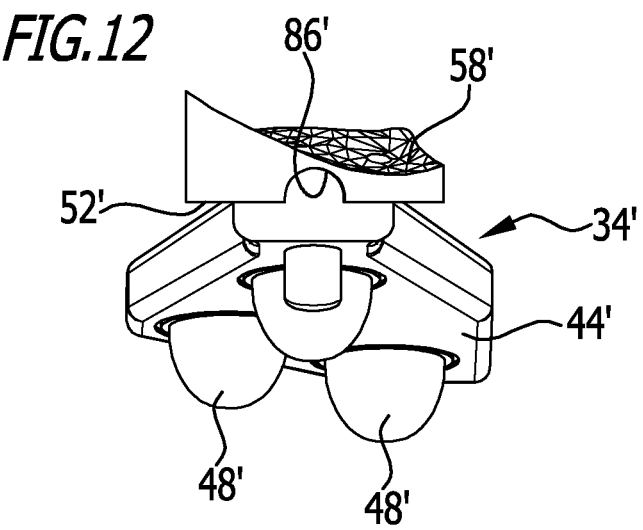
FIG. 12 illustrates a view of the referencing unit taken in the direction of arrow B in FIG. 11.
Figure 13:
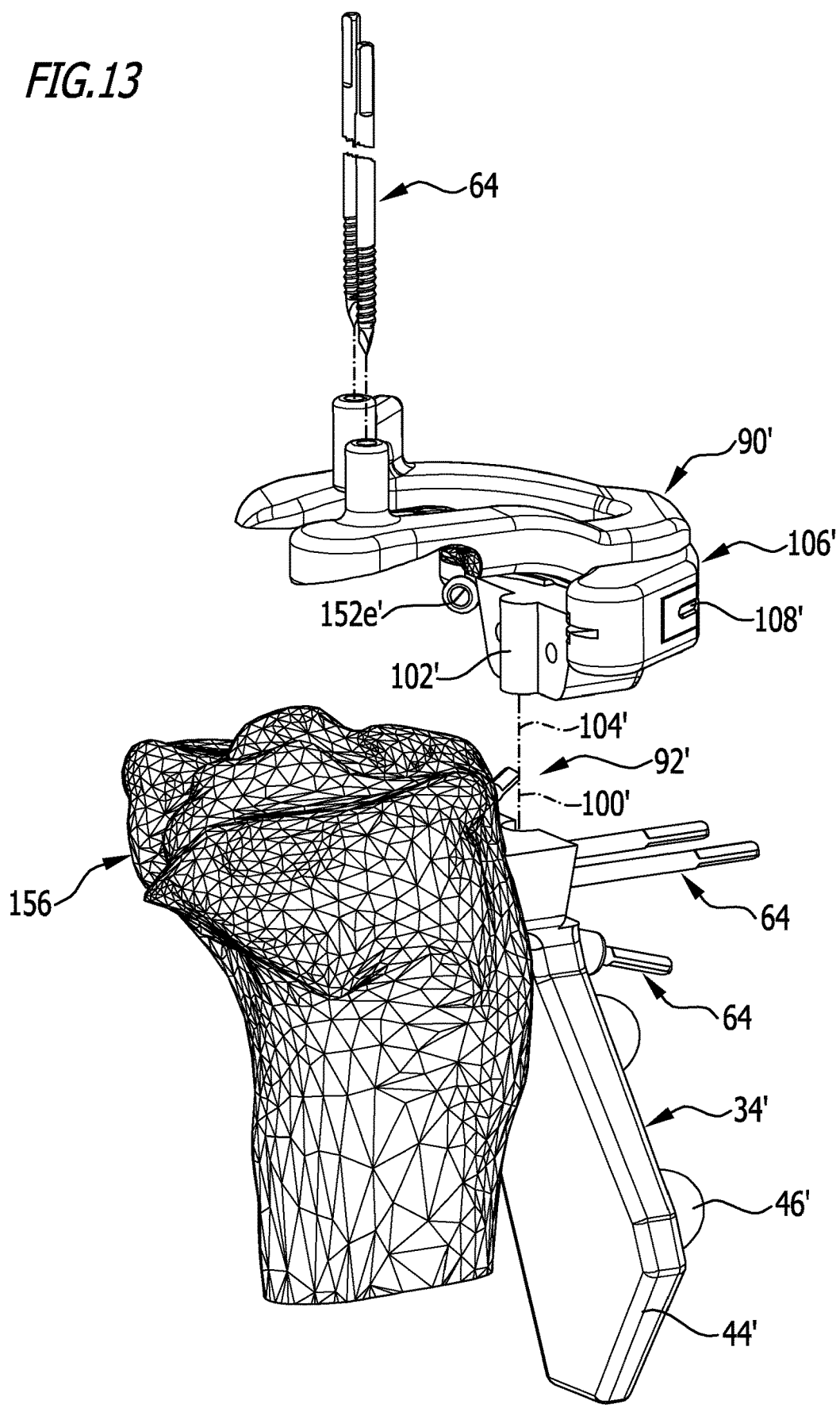
FIG. 13 illustrates a schematic general view of the referencing unit of FIG. 10 and of another exemplary embodiment of a medical instrument prior to coupling and fixing thereof to the tibia.
Figure 14:
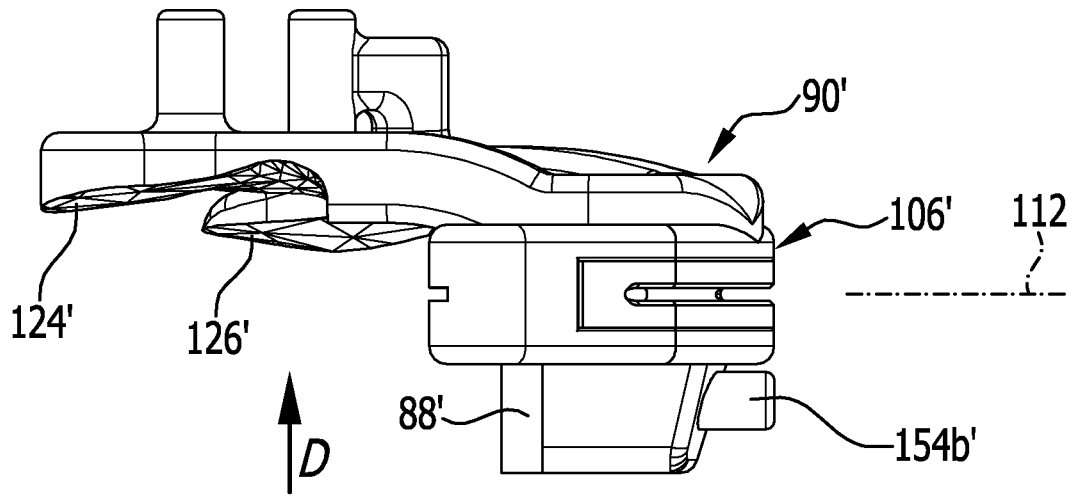
FIG. 14 illustrates a side view of the medical instrument taken in the direction of arrow C in FIG. 15.
Figure 15:
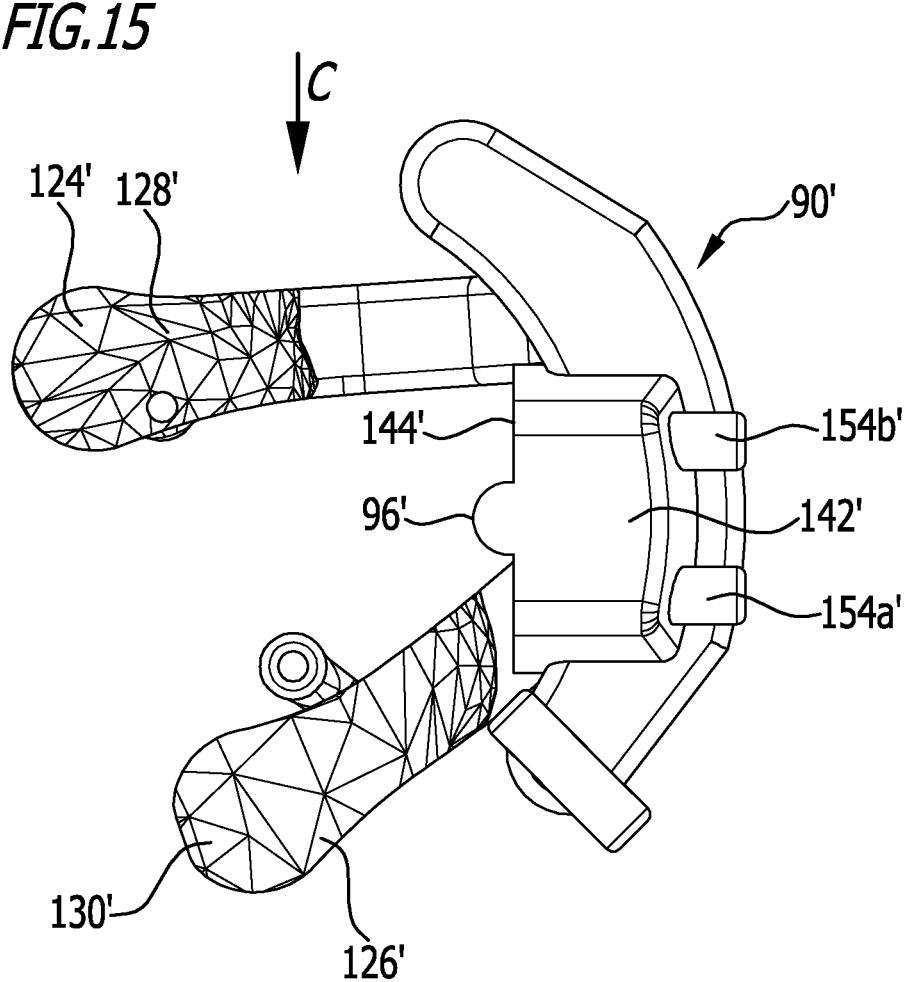
FIG. 15 illustrates a bottom view of the instrument of FIG. 14 taken in the direction of arrow D.

Optionally or alternatively, the medical system comprises a further referencing unit 34', schematically shown in FIG. 10 before being placed in contact against a tibia 156.

The referencing unit 34' comprises a base body 38' which carries a carrier element 40' comprising marker elements 42'. In the referencing unit 34' as illustrated in FIG. 10, the carrier element 40' is configured in the form of a polygonal carrier plate 44' on which the marker elements 42' are arranged. These are configured in the form of hemispheres 46' whose surfaces 48' reflect electromagnetic radiation or ultrasound.

Alternatively, instead of being implemented in a passive configuration as described above, the marker elements 42' may also be configured in the form of active marker elements which emit for example electromagnetic radiation or ultrasound.

The arrangement of the marker elements 42' relative to each other is preferably stored in a storage of the data processing equipment 20. The position of the individual marker elements 42' in space and thus the location and orientation of the referencing unit 34' as a whole can then be determined by way of the navigation system 12 in a known manner.

In the referencing unit 34' of FIG. 10, the base body 38' and the carrier element 40' are non-releasably connected together. Alternatively, they can be configured in one piece.

The base body 38' has a planar upper side 52' and a bottom side 54'. The bottom side 54' is configured in the form of a patient-specific bone contact face 56' that faces away from the base body 38' and deviates from being a sector of a surface of a sphere and from being a planar surface. A contour 58' of the bone contact face 56' corresponds to a part 61' of a bone surface 60' of the tibia 156.

Based on the contour 58' of the bone contact face 56' that is adapted to the bone surface 60', there exists exactly one possibility of placing the base body 38' in contact against the tibia 156 in a precisely fitting relationship therewith. That position of the referencing unit 34' on the tibia 156 is illustratively depicted in FIG. 10.

Furthermore, the referencing unit 34' is provided with fastening element receptacles 62*a'*, 62*b'* and 62*c'*. Each of these serves to receive a fastening element 64 for fixing the referencing unit 34' to the tibia 156.

The fastening element receptacles 62*a'*, 62*b'* and 62*c'* are configured in the form of openings 66*a'*, 66*b'* and 66*c'*, namely in the form of bores 68*a'*, 68*b'* and 68*c'*. The bores 68*a'* and 68*b'* extend transversely, in particular perpendicularly, to the upper side 52' and extend through the bone contact face 56'.

The bore 68*c'* is formed in the area of the carrier plate 44' and extends through the carrier element 40'. The opening 66*c'* of the carrier plate 44 is somewhat extended by way of a sleeve 72' projecting from an upper side 70' of the carrier element 40', said sleeve 72' defining a longitudinal axis that extends in skew relation to the longitudinal axes of the bores 68*a'* and 68*b'*.

For fixing the referencing unit 34' to the tibia 156, further fastening elements 64 are used, these being in the form of bone pins 74.

An external diameter of the shaft section 80 of the bone pins 74 is also adapted to an internal diameter of the bores 68*a'*, 68*b'* and 68*c'* so that the bone pins 74 can extend with the shaft section 80 thereof through the openings 66*a'*, 66*b'* and 66*c'* in a manner essentially free from play.

Furthermore, the base body 38' has formed thereon a first coupling element 86' which corresponds to a second coupling element 88' of a medical instrument 90'. The coupling elements 86' and 88' form a coupling device 92' for force-locking and/or form-locking coupling of the medical instrument 90' and the referencing unit 34' in a coupling position.

The first coupling element 86' is in the form of a coupling receptacle 94', and the second coupling element 88' is in the form of a corresponding coupling projection 96' cooperating therewith. The coupling receptacle 94' is configured in the form of a groove defining a longitudinal axis 100', said groove defining a cross-section of semi-circular shape. The coupling projection 96' is configured in the form of a rib 102' of semi-cylindrical shape whose longitudinal axis 104' runs parallel to the longitudinal axis 100'.

The instrument 90' comprises a saw template 106' for a tibia 156. The saw template 106' comprises a saw slot 108' which defines a cutting plane 112.

The instrument 90' further comprises a substantially U-shaped contact body 116' which carries, in a connecting area between free legs of the contact body 116', a projecting slot body 120' through which the saw slot 108' extends.

Formed on a rear side 122' of the contact body 116', in the area of free ends thereof, are two contact body bone contact faces 124' and 126' having contours 128' and 130' which correspond to portions or parts 132' and 134' of the bone surface 60' of the tibia 156.

Formed on the slot body 120' is a coupling body 142' having a planar bottom side 144' from which the coupling projection 96' projects. The coupling body 142' is substantially configured in the shape of a cuboid.

The bottom side 144' is in surface contact against the upper side 52' of the base body 38' when in the coupling position.

Furthermore, the coupling body 142' has two instrument fastening element receptacles 148a' and 148b' which are configured in the form of openings 150a' and 150b', namely in the form of bores 152a' and 152b'.

Figure 16:
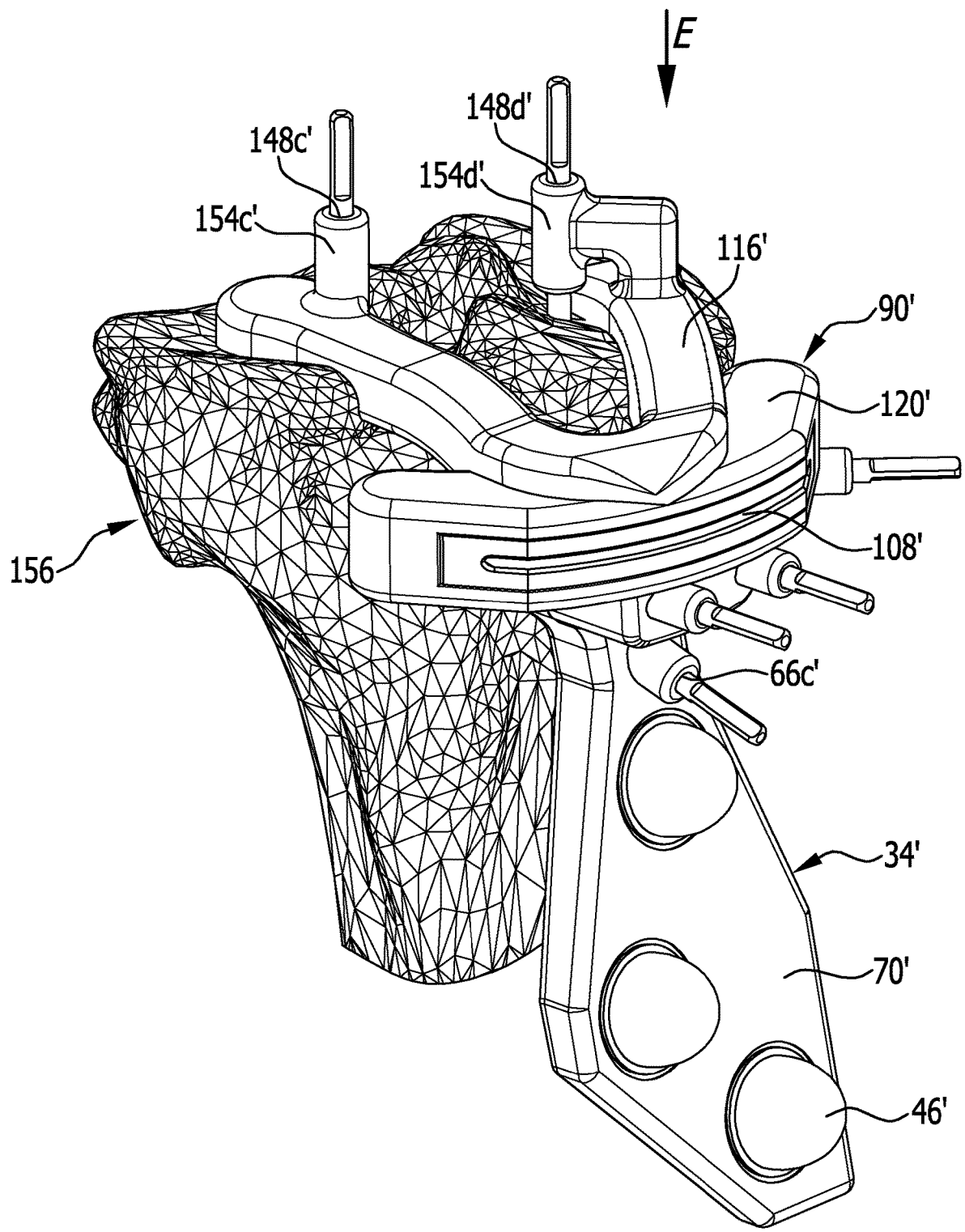
FIG. 16 illustrates a schematic general view of the unit of the medical instrument and referencing unit from FIG. 13 after fixing to the tibia.
Figure 17:
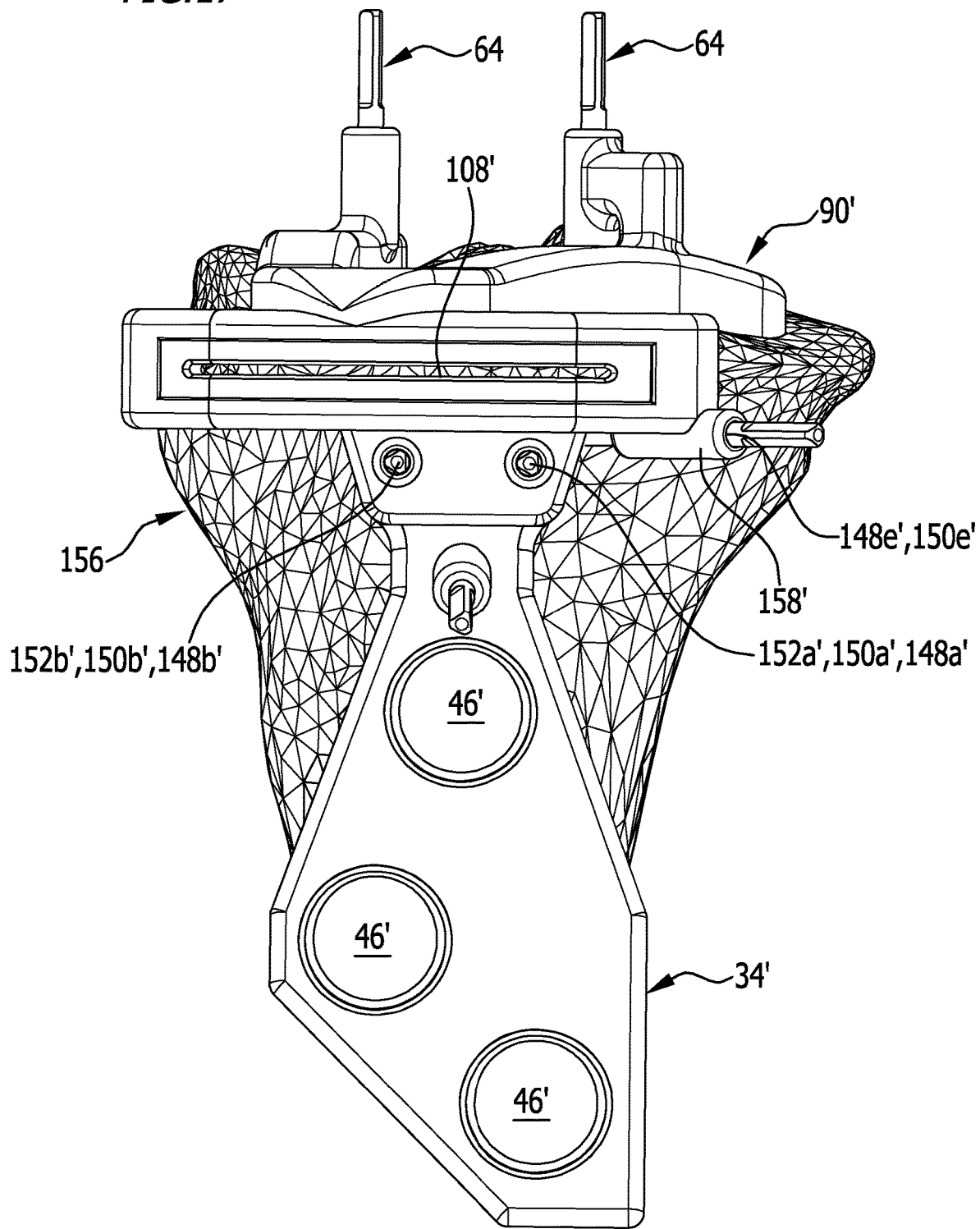
FIG. 17 illustrates a view of the arrangement from FIG. 16 seen from anterior.
Figure 18:
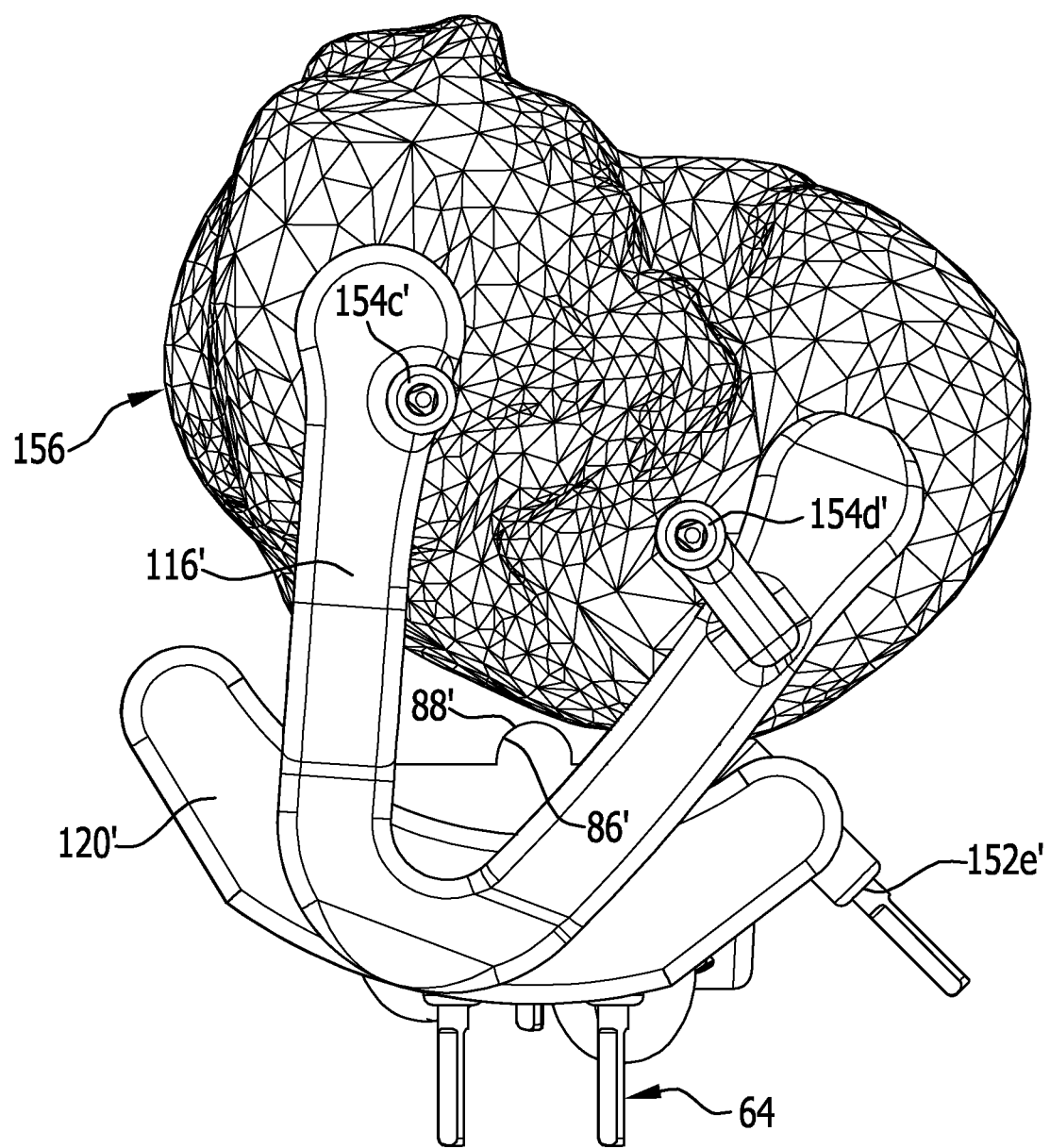
FIG. 18 illustrates a view of the arrangement in FIG. 16 taken in the direction of arrow E.

In the coupling position, longitudinal axes of the bores 152a' and 152b' coincide with longitudinal axes of the bores 68a' and 68b'. This allows for the referencing unit 34' and the instrument 90' to be fixed to the tibia 156 by way of two fastening elements 64 when in the coupling position. This is schematically depicted in FIGS. 16 to 18.

In order to be able to additionally fix the instrument 90' to the tibia 156, the contact body 116' has provided thereon two further instrument fastening element receptacles 148c' and 148d' which extend through the contact body bone contact faces 124' and 126'.

Formed on the slot body 120' is a further instrument fastening element receptacle 148e', namely in the form of an opening 150e' of a sleeve 158. The opening 150e' is configured in the form of a bore 152e' of the sleeve 158.

The instrument fastening element receptacles 148a', 148b', 148c' and 148d' are also extended by or formed in short sleeves 154a', 154b', 154c' and 154d'. Longitudinal axes of the instrument fastening element receptacles 148c' and 148d' extend essentially parallel to each other and define a plane that extends perpendicularly to a plane spanned by longitudinal axes of the instrument fastening element receptacles 148a' and 148b'. The last-named plane further extends parallel to the cutting plane 112'.

The patient-specific bone contact face 56' defines bone contact face contour data that correspond to non-invasively determined bone contour data of the patient. To this end, in particular, the patient's bone contour data from X-ray, magnetic resonance and/or ultrasound images can be utilized.

Based on the patient's bone contour data thus determined in a non-invasive manner, the patient-specific bone contact face 56' or the base body 38' can be manufactured by, for example, casting, chip-producing machining methods or 3-D printing. Thus, this means that for the surgical intervention, a base body 38' is configured that is individually adapted to a contour of the patient's tibia 156. The non-invasively determined bone contour data of the patient thus result in a unique positioning of the referencing unit 34' on the tibia 156.

The contact body 116', or the entire instrument 90', with the contact body bone contact faces 124' and 126' thereof is also configured analogously to what has been described above. The patient-specific contact body bone contact face defines contact body bone contact face contour data that correspond to non-invasively determined bone contour data of the patient.

These bone contour data of the patient, too, can be derived in particular from X-ray, magnetic resonance and/or ultrasound images.

Overall, it is thus possible to provide for unique positioning of the instrument 90' on the tibia 156. Moreover, because the coupling device 92' predetermines a unique spatial relationship between the referencing unit 34' and the instrument 90' when in the coupling position, the cutting plane 112' predetermined by the surgeon, in particular on the basis of the non-invasively determined image data, are defined uniquely and individually for the respective patient by way of the saw slot 108'.

The fixing of the referencing unit 34' and the medical instrument 90' for preparation of the tibia 156 for implantation of a tibial component of a knee joint endoprosthesis is explained below.

First, the referencing unit 34' is brought with the bone contact face 56' thereof to the part 61' of the bone surface 60' so that the referencing unit 34' is in contact against the tibia 156 in a unique manner. The referencing unit 34' is pre-fixed to the tibia 156 using two bone pins 74. To this end, the bone pins 74 are inserted through the fastening element receptacles 62a' and 62b'.

Optionally, in order to additionally prevent rotation of the referencing unit 34' relative to the tibia 156, a further bone pin 74 can be inserted through the fastening element receptacle 62c' and driven into the tibia 156. This is recommendable in particular where the referencing unit 34' is to be used by itself, i.e. without the instrument 90', for example for determining a location and orientation of the tibia 156 in space.

Via the bone pins 74 projecting from the tibia 156 in parallel relation to each other and extending through the openings 66a' and 66b', it is now possible for the instrument 90' to be brought to the tibia 156. To this end, the coupling body 142' is brought to the polygonal sections 82 of the bone pins 74 previously set in position, and these are then passed through the bores 152a' and 152b'.

In order to prevent displacement of the instrument 90' relative to the tibia 156 and to the referencing unit 34', two further bone pins 74 are inserted through the instrument fastening element receptacles 148c' and 148d' and anchored in the tibia 156.

In order to carry out a saw cut on the tibia 156 using the instrument 90', the referencing unit 34' can be optionally removed from the tibia 156 without the instrument 90' having to be removed. To this end, the two bone pins 74 that extend through the bores 152a' and 152b' are removed from the tibia 156 so that the referencing unit 34' can be withdrawn from between tibia 156 and contact body 116'.

Alternatively, it is also possible for the instrument 90' and the referencing unit 34' to be configured such that the instrument 90' is capable of being removed from the tibia 156 so that the referencing unit 34' alone can remain in place on the tibia 156 in order, for example, to continue tracking the location and orientation thereof in space. To this end, in particular once the saw cut has been made, the instrument 90' can, after removing the bone pins 74 inserted through the instrument fastening element receptacles 148e', 148c' and 148d', be removed from the tibia 156 and from the two bone pins 74 inserted through the instrument fastening element receptacles 148a' and 148b'. The referencing unit 34' then remains in what is called a "parked" position.

Optionally, the instrument 90' and the referencing unit can be placed in contact against the tibia 156 together instead of in the order described.

Alternatively, it is also possible to first place instrument 90' with the contact body bone contact faces 124' and 126' thereof into contact against the tibia 156 and fix it thereto and only then couple the instrument 90' to the referencing unit 34'.

For a good fixation of the instrument 90' to the tibia 156, the two bone pins 74 that had been removed can be inserted again. Alternatively or additionally, it is also possible for a bone pin 74 to be inserted through the bore 152e' and anchored in the tibia 156, wherein a longitudinal axis of the bore 152e' extends at a skew angle relative to the longitudinal axes of the bores 152a' and 152b'.

After the desired cuts have been made on the tibia 156 with a saw, all of the bone pins 74 and the medical instrument 90' can be removed again from the tibia 156.

It is possible for the instrument 90' to be replaced with a further instrument, not shown in the figures, in order to carry out further saw cuts on the tibia 156.

With the tibia 156 now prepared, a tibial component of a knee joint endoprosthesis, not illustrated in the figures, can be placed thereagainst and suitably affixed thereto, for example by way of bone screws and/or bone cement.

Both the referencing unit 34' and the medical instrument 90' may be made entirely from a sterilizable plastics material, such as polyetheretherketone (PEEK).

Optionally, it is also conceivable for the base body 38' and the carrier element 40' to be configured for releasable connection to one another. To that end, there may be provided a coupling device, not depicted in the figures, comprising first and second coupling elements which are arranged or formed on the base body 38' on the one hand and on the carrier element 40' on the other hand. This then allows for the base body 38' and the carrier element 40' to be temporarily connected together in a manner similar to the coupling device 92'. In particular, this makes it possible for the carrier element 40' with the marker elements 42' thereon to be separated from the base body 38'. Thus, for example, the carrier element 40' with the marker elements 42 thereon can be used multiple times and only the base body 38' with the patient-specific bone contact face 56' thereof need be fabricated in a patient-specific manner for the surgical intervention. It is thus possible to additionally reduce costs.

What is claimed is:

1. A medical system, in particular for implanting a knee joint endoprosthesis, comprising:
    at least one medical referencing unit whose position in space is detectable using a surgical navigation system, which at least one medical referencing unit comprises:
        (a) at least one surgical marker element that is directly arranged or formed on a carrier element and is detectable using a detection device of the surgical navigation system, and
        (b) a base body that carries the carrier element, and
    at least one medical instrument which is releasably connectable to the at least one referencing unit, wherein:
        the base body comprises at least one patient-specific bone contact face facing away from the base body and deviating from being a sector of a surface of a sphere and from being a planar surface, said at least one bone contact face being formed in a manner corresponding to a bone surface of the patient, and
        the base body and the carrier element are of a one-piece monolithic configuration or are non-releasably connected together such that the base body and the carrier element can be disconnected only by destroying at least one of the base body and the carrier element,
        the at least one medical instrument comprises at least one of a saw template for a femur and a saw template for a tibia,
        the at least one of a saw template for a femur and a saw template for a tibia comprises at least one saw slot for guiding a saw blade of a bone saw when the saw template is coupled to the at least one referencing unit.

2. The medical system in accordance with claim 1, wherein the base body and the carrier element are non-releasably connected together, the medical system further comprising a coupling device for only a single or unique coupling of the base body and the carrier element in a coupling position in at least one of a form-fit or force-fit arrangement, wherein:
    the coupling device comprises first and second coupling elements which are arranged or formed on the base body on the one hand and the carrier element on the other hand and are in engagement when in the coupling position and are out of engagement when in an uncoupling position, and
    the first and second coupling elements comprise at least one coupling receptacle and a corresponding coupling projection cooperating therewith.

3. The medical system in accordance with claim 1, wherein the at least one referencing unit comprises at least one fastening element receptacle for a fastening element for fixing the referencing unit to a bone.

4. The medical system in accordance with claim 3, wherein the at least one fastening element receptacle is at least one of:
    a) arranged or formed on at least one of the base body and the carrier element,
    b) configured in the form of an opening.

5. The medical system in accordance with claim 1, further comprising one of:
    a) a coupling device for at least one of force-locking and form-locking coupling of the at least one medical instrument and the at least one referencing unit in a coupling position, or
    b) a coupling device for at least one of force-locking and form-locking coupling of the at least one medical instrument and the at least one referencing unit in a coupling position, wherein the coupling device comprises first and second coupling elements which are arranged or formed on the at least one referencing unit on the one hand, in particular on the base body, and on the at least one medical instrument on the other hand and are in engagement when in the coupling position and are out of engagement when in an uncoupling position.

6. The medical system in accordance with claim 1, further comprising
    a) at least one medical instrument which is releasably connectable to the at least one referencing unit, wherein the at least one medical instrument comprises at least one instrument fastening element receptacle for a fastening element for fixing the at least one medical instrument to a bone, or b) at least one medical instrument which is releasably connectable to the at least one referencing unit, and a coupling device for at least one of force-locking and form-locking coupling of the at least one medical instrument and the at least one referencing unit in a coupling position, wherein the at least one medical instrument comprises at least one instrument fastening element receptacle for a fastening element for fixing the at least one medical instrument to a bone.

7. The medical system in accordance with claim 6, wherein the at least one instrument fastening element receptacle is configured in the form of an opening, in particular in the form of a bore.

8. The medical system in accordance with claim 5, wherein the at least one medical instrument comprises a contact body comprising at least one patient-specific contact body bone contact face facing away from the contact body and deviating from being a sector of a surface of a sphere and from being a planar surface, said at least one patient-specific contact body bone contact face being formed in a manner corresponding to a bone surface of the patient.

9. The medical system in accordance with claim 5, wherein:
the at least one referencing unit comprises at least one fastening element receptacle for a fastening element for fixing the referencing unit to a bone, and
the at least one fastening element receptacle and the at least one instrument fastening element receptacle each define a longitudinal axis, said longitudinal axes coinciding in the coupling position.

10. The medical system in accordance with claim 8, wherein the patient-specific bone contact face and/or the patient-specific contact body bone contact face have a contour which corresponds to at least a part of a bone surface of a femur or of a tibia.

11. The medical system in accordance with claim 1, wherein:
the at least one medical instrument comprises a contact body comprising at least one patient-specific contact body bone contact face facing away from the contact body and deviating from being a sector of a surface of a sphere and from being a planar surface, said at least one patient-specific contact body bone contact face being formed in a manner corresponding to a bone surface of the patient, and at least one of:
a) at least one of the patient-specific bone contact face and the patient-specific contact body bone contact face and the base body and the contact body are manufactured by casting, molding, chip-producing machining methods or 3-D printing, and
b) the patient-specific bone contact face defines bone contact face contour data which correspond or substantially correspond to non-invasively determined bone contour data of the patient.

12. The medical system in accordance with claim 8, wherein the patient-specific contact body bone contact face defines contact body bone contact face contour data that correspond or substantially correspond to non-invasively determined bone contour data of the patient, in particular bone contour data of the patient from X-ray, magnetic resonance and/or ultrasound images.

13. The medical system in accordance with claim 1, further comprising at least one of:
a) at least one fastening element for fixing the referencing unit to a bone, and
b) a surgical navigation system comprising at least one detection device for detecting the position of the at least one referencing unit.

14. The medical system in accordance with claim 13, wherein the least one fastening element is configured in the form of a bone screw or in the form of a bone pin or in the form of a bone nail.

15. The medical system in accordance with claim 1, wherein the least one referencing unit comprises at least three marker elements.

16. A medical system, in particular for implanting a knee joint endoprosthesis, comprising:
at least one medical referencing unit whose position in space is detectable using a surgical navigation system, which at least one medical referencing unit comprises:
at least one surgical marker element that is arranged or formed on a carrier element and is detectable using a detection device of the surgical navigation system, and
a base body that carries the carrier element,
wherein the base body comprises at least one patient-specific bone contact face facing away from the base body and deviating from being a sector of a surface of a sphere and from being a planar surface, said at least one bone contact face being formed in a manner corresponding to a bone surface of the patient,
further comprising at least one medical instrument which is releasably connectable to the at least one referencing unit,
wherein:
the at least one medical instrument comprises a saw template for at least one of a femur and a tibia, and
the saw template comprises at least one saw slot for guiding a saw blade of a bone saw when the saw template is coupled to the at least one medical referencing unit.

17. The medical system in accordance with claim 16, further comprising a coupling device for at least one of force-locking and form-locking coupling of the at least one medical instrument and the at least one referencing unit in a coupling position.

18. The medical system in accordance with claim 16, wherein the base body and the carrier element are of one-piece configuration or are non-releasably connected together.

19. The medical system in accordance with claim 16, wherein the base body and the carrier element are configured for releasable connection to each other.

20. The medical system in accordance with claim 17, wherein the coupling device comprises first and second coupling elements which are arranged or formed on the at least one referencing unit on the one hand, in particular on the base body, and on the at least one medical instrument on the other hand and are in engagement when in the coupling position and are out of engagement when in an uncoupling position.

* * * * *

UNITED STATES PATENT AND TRADEMARK OFFICE
CERTIFICATE OF CORRECTION

PATENT NO. : 10,675,096 B2
APPLICATION NO. : 15/358799
DATED : June 9, 2020
INVENTOR(S) : Utz et al.

Page 1 of 1

It is certified that error appears in the above-identified patent and that said Letters Patent is hereby corrected as shown below:

In the Claims

Column 17, Line 26:
"9. The medical system in accordance with claim 5,"
Should read:
-- 9. The medical system in accordance with claim 6, --

Signed and Sealed this
Thirteenth Day of October, 2020

Andrei Iancu
*Director of the United States Patent and Trademark Office*